United States Patent
Van Berge et al.

(10) Patent No.: US 6,835,690 B2
(45) Date of Patent: Dec. 28, 2004

(54) COBALT CATALYSTS

(75) Inventors: Peter Jacobus Van Berge, Sasolburg (ZA); Jan Van De Loosdrecht, Sasolburg (ZA); Jacobus Lucas Visagie, Sasolburg (ZA)

(73) Assignee: Sasol Technology Limited, Johannesburg (ZA)

( * ) Notice: Subject to any disclaimer, the term of this patent is extended or adjusted under 35 U.S.C. 154(b) by 0 days.

(21) Appl. No.: 10/306,875

(22) Filed: Nov. 27, 2002

(65) Prior Publication Data

US 2003/0211940 A1 Nov. 13, 2003

Related U.S. Application Data

(63) Continuation of application No. PCT/IB01/01012, filed on Jun. 11, 2001.
(60) Provisional application No. 60/210,986, filed on Jun. 12, 2000, and provisional application No. 60/215,489, filed on Jun. 30, 2000.

(51) Int. Cl.$^7$ .......................... B01J 21/08; B01J 23/40; B01J 23/42; B01J 23/58; B01J 23/56
(52) U.S. Cl. ..................... 502/328; 502/243; 502/252; 502/260; 502/326; 502/327; 502/330; 502/332; 502/333; 502/334; 502/339
(58) Field of Search ................... 502/260, 243, 502/252, 326, 327, 328, 330, 332, 333, 334, 339, 350, 351, 355, 407, 415, 439, 242, 263

(56) References Cited

U.S. PATENT DOCUMENTS 3,617,509 A * 11/1971 Hensley, Jr. ............... 208/111
4,046,672 A * 9/1977 Pollitzer et al. ............ 208/139
4,085,067 A * 4/1978 Pollitzer et al. ............ 252/442
4,136,064 A * 1/1979 Hayes et al. ............ 252/466 B
4,280,930 A * 7/1981 Antos .................... 252/466 B
5,053,574 A   10/1991 Tsutsui et al. .............. 585/488
5,545,674 A    8/1996 Behrmann et al. .......... 518/715
5,733,839 A    3/1998 Espinoza et al. ........... 502/336
5,856,365 A    1/1999 Zennaro et al. ............ 518/715

FOREIGN PATENT DOCUMENTS

| EP | 0069514 | 1/1983 |
| EP | 0681868 | 11/1995 |
| GB | 1105157 | 3/1968 |
| WO | 9942214 | 8/1999 |
| WO | 0020116 | 4/2000 |
| WO | 01/39882 A1 | 6/2001 |

OTHER PUBLICATIONS

Knözinger, H. and P. Ratnasamy. "Catalytic Aluminas: Surface Models and Characterization of Surfac Sites", *Catal. Rev. –Sci. Eng.*, (1978), 17(1): 31–70, Presented at the Fifth North American Meeting of the Catalysis Society, Pittsburgh, 1977.

* cited by examiner

*Primary Examiner*—Cam N. Nguyen
(74) *Attorney, Agent, or Firm*—Ladas & Parry

(57) ABSTRACT

A cobalt based Fischer-Tropsch catalyst which including a porous catalyst support and metallic cobalt crystallites within the support. The catalyst has a proportion of its cobalt in reducible form, with this proportion being expressible as $\Omega$ mass %, based on the total pre-reduction catalyst mass. The catalyst also has, when freshly reduced, a mono-modal Gaussian metallic cobalt crystallite size distribution, a metallic cobalt surface area, in m$^2$ per gram of catalyst, of from 0.14 $\Omega$ to 1.03 $\Omega$, and a catalyst geometry that ensures a stabilized Fischer-Tropsch synthesis effectiveness factor of 0.9 or greater.

28 Claims, 11 Drawing Sheets

Superimposition of the Relative Intrinsic Activity Factor (R.I.A.F.) profiles of 5 selected micro slurry phase CSTR Fischer-Tropsch synthesis runs performed on catalyst B

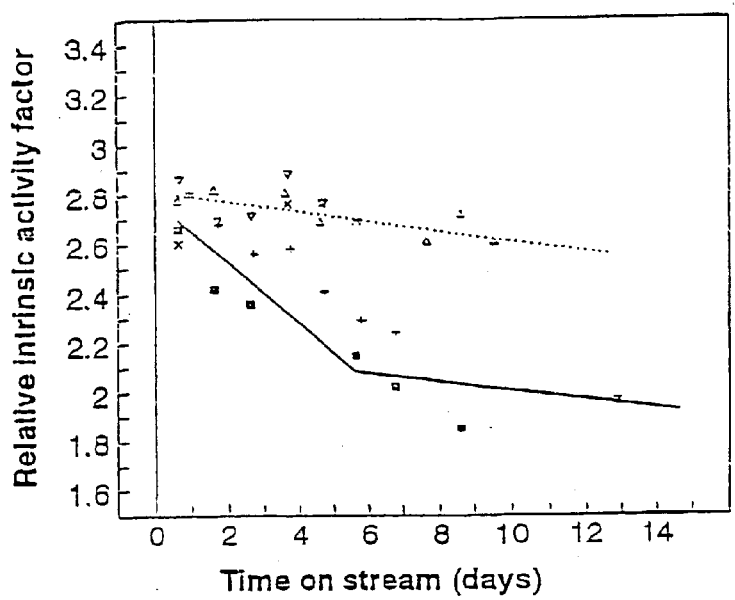

- ■ Synthesis run number 106F
- ∻ Synthesis run number 29F
- △ Synthesis run number 317$
- × Synthesis run number 319$
- ▽ Synthesis run number 215F ——— Modelled deactivation profile, based on the following parameter values:
  $t_i$ = 15 hours
  $a_i$ = 2.7
  Duration of phase 2 deactivation = 5 days
  % drop in $a_i$ due to rejuvenatable deactivation = 20
  % drop in $a_i$ due to oxidation ≥ 5
  Deactivation rate due to oxidation (ex $t_i$) = 0.0111 units/day
  APG space velocity = 0.04 $dm_n^3$ /(g catalyst.min)

·········· Modelled deactivation profile, based on the following parameter values:
  $t_i$ = 15 hours
  $a_i$ = 2.8
  Complete absence of rejuvenatable deactivation
  % drop in $a_i$ due to oxidation ≥ 5
  Deactivation rate due to oxidation (ex $t_i$) = 0.0111 units/day
  APG space velocity = 0.07 $dm_n^3$ /(g catalyst.min)

FIG 3

Proposed bi-modal Gaussian crystallite population present in the freshly reduced 30gCo/100gAl$_2$O$_3$ catalyst B Note: Chosen model parameter values $\mu_1 = 6.0 \qquad \sigma_1 = 1.0$ $\mu_2 = 16.0 \qquad \sigma_2 = 5.0$ $\beta = 0.976$ \* Note: As derived from equation (1)

Proposed bi-modal Gaussian probability distribution of the metallic cobalt cobalt content of the freshly reduced $30gCo/100gAl_2O_3$ catalyst B Note: Chosen model parameter values $\mu_1 = 6.0 \qquad \sigma_1 = 1.0$ $\mu_2 = 16.0 \qquad \sigma_2 = 5.0$ $\beta = 0.976$

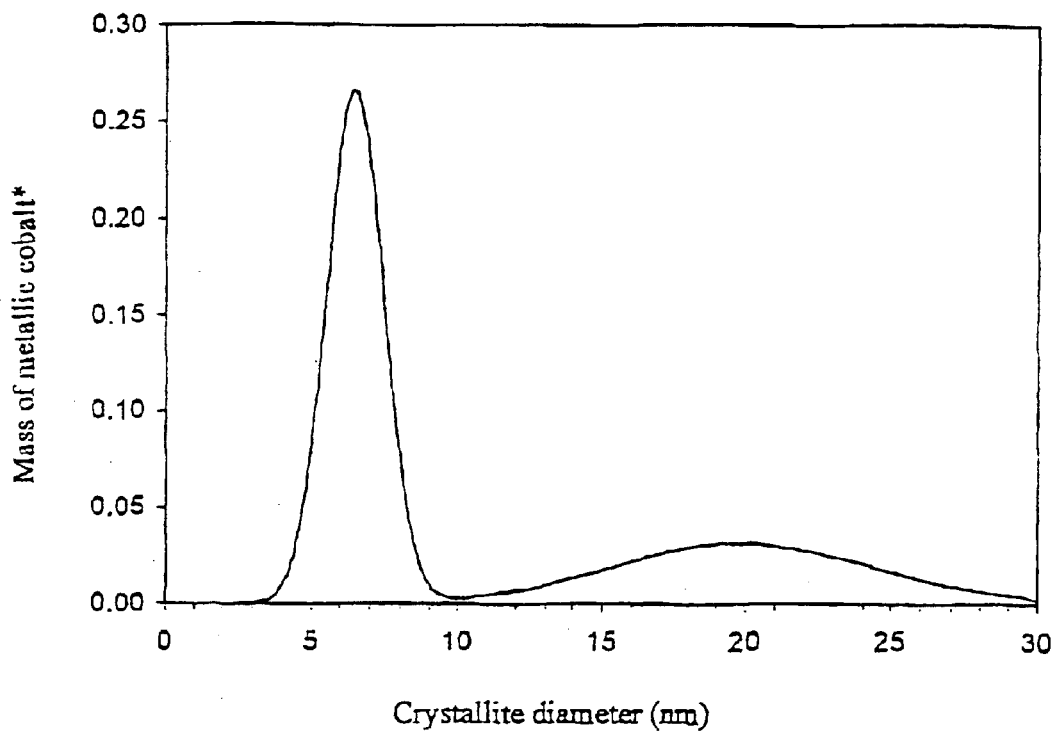

* Note: As derived from equations (5) and (6), i.e.:

$$\left[ \frac{x^3(\beta g_{\mu_1,\sigma_1}(x) + (1-\beta)g_{\mu_2,\sigma_2}(x))}{\left[ \int_0^\infty x^3(\beta g_{\mu_1,\sigma_1}(x) + (1-\beta)g_{\mu_2,\sigma_2}(x)) \, dx \right]} \right]$$

FIG 5

Illustration of the postulated influence of oxidation as deactivation mechanism during slurry phase Fischer-Tropsch operation under realistic synthesis conditions (i.e. 220°C; 20 bar; feed gas composition: 50 vol% $H_2$ + 25 vol% CO; %($H_2$ + CO) conversion: 50-70%) as applied to the $30gCo/100gAl_2O_3$ catalyst B

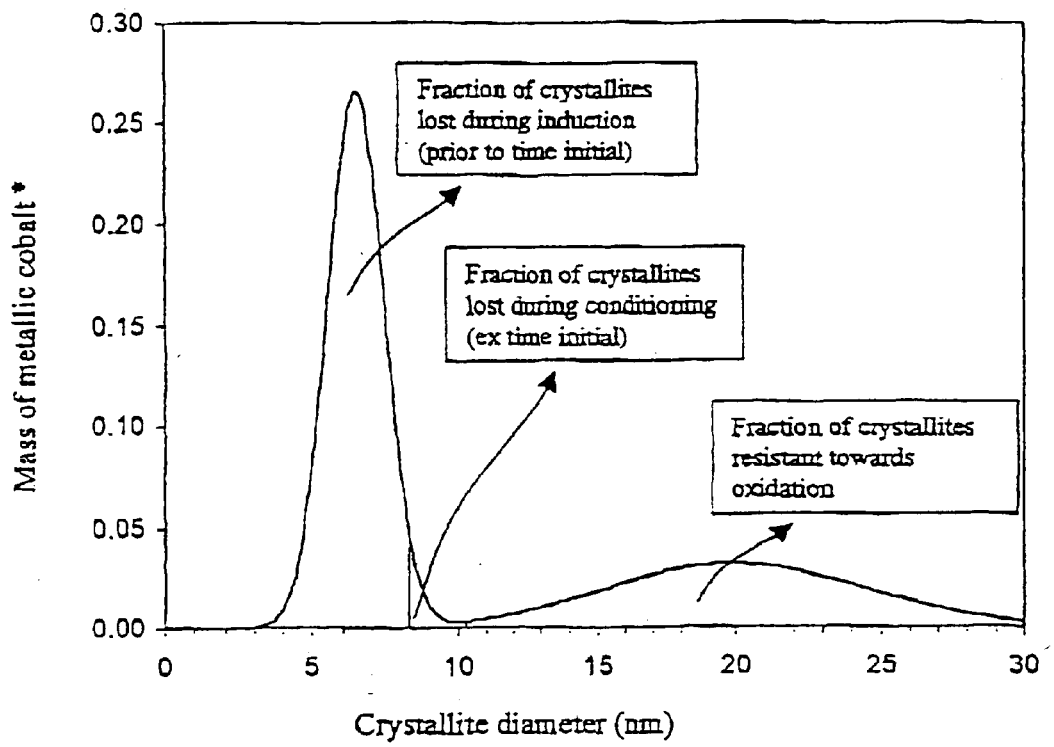

* Note: As derived from equations (5) and (6), i.e.:

$$\left[ \frac{x^3 (\beta g_{\mu_1,\sigma_1}(x) + (1-\beta)g_{\mu_2,\sigma_2}(x))}{\left[ \int_0^\infty x^3 (\beta g_{\mu_1,\sigma_1}(x) + (1-\beta)g_{\mu_2,\sigma_2}(x))\, dx \right]} \right]$$

FIG 6

Relationship between the Relative Intrinsic (Fischer-Tropsch) Activity Factors and the specific metallic cobalt surface area of freshly reduced supported 19.5 mass% cobalt catalysts, displaying a mono-modal Gaussian Crystallite Size Distribution □ R.I.A.F. at time zero
+ Initial activity (a_i)
♦ Stabilized R.I.A.F.

Relationship between the Relative Intrinsic (Fischer-Tropsch) Activity Factors and the specific metallic cobalt surface area of freshly reduced supported cobalt catalysts (containing a metal loading of $\Omega$ mass% reducible cobalt) displaying a mono-modal Gaussian Crystallite Size Distribution □ R.I.A.F. at time zero
+ Initial activity ($a_i$)

Superimposition of the Temperature Programmed Reduction profiles of the finally calcined catalyst precursors of catalyst B, of composition: 30g Co/ 0.075g Pt/100g Al₂O₃ and catalyst F (A linear programmed heating rate of 10°C/minute and a feed gas composition of: 10 vol% H₂ in argon was utilised at a dynamic flow rate of 1,6 ± 0,4 ml$_{(n)}$/(mg catalyst.minute)).

Superimposition of the Temperature Programmed Reduction profiles of the finally calcined catalyst precursors of catalyst B, of composition: 30g Co/ 0.075g Pt/100g Al$_2$O$_3$ and catalyst E (A linear programmed heating rate of 10°C/minute and a feed gas composition of: 10 vol% H$_2$ in argon was utilised at a dynamic flow rate of 1,6 ± 0,4 ml$_{(n)}$/(mg catalyst.minute)).

Superimposition of the Temperature Programmed Reduction profiles of the finally calcined catalyst precursors of catalyst B, of composition: 30g Co/ 0.075g Pt/100g Al$_2$O$_3$ and catalyst G (A linear programmed heating rate of 10°C/minute and a feed gas composition of 10 vol% H$_2$ in argon was utilised at a dynamic flow rate of 1,6 ± 0,4 ml$_{(n)}$/(mg catalyst.minute)).

The correlation between observed initial relative intrinsic activity factors (i.e. $a_i$) of $Co/Al_2O_3$ slurry phase Fischer-Tropsch catalyst prepared according to method B and the total $Co(NO_3)_2 \cdot 6H_2O$ loading per $m^2$ of SASOL Germany GmbH's product: Puralox SCCa 5/150

20 # COBALT CATALYSTS

This application is a continuation of PCT/IB01/01012 filed Jun. 11, 2000 which claims benefit of No. 60/210,986 filed Jun. 12, 2000 and claims benefit of No. 60/215,489 filed Jun. 30, 2000.

FIELD OF THE INVENTION

THIS INVENTION relates to cobalt catalysts. In particular, the invention relates to a cobalt based Fischer-Tropsch catalyst, to a precursor of such a cobalt catalyst, to a process for preparing a precursor of such a cobalt catalyst, to a process for preparing such a cobalt catalyst, and to a process for producing hydrocarbons using such a cobalt catalyst.

BACKGROUND OF THE INVENTION

The Applicant is aware of known processes for preparing cobalt based catalyst precursors and which involve slurry phase impregnation of a catalyst support with a cobalt salt, drying of the impregnated catalyst support, and calcination of the dried impregnated catalyst support, to achieve a desired cobalt loading of the support. The resultant precursors are then activated by reduction thereof, to obtain cobalt based Fischer-Tropsch catalysts. These catalysts can display good intrinsic activities when used for Fischer-Tropsch synthesis; however, catalysts having enhanced or superior intrinsic activities cannot readily be obtained using the known processes. It is thus an object of the present invention to provide a cobalt based Fischer-Tropsch catalyst having enhanced initial and/or stabilized intrinsic Fischer-Tropsch synthesis activity, as well as a process for preparing such a catalyst.

SUMMARY OF THE INVENTION

According to a first aspect of the invention, there is provided a cobalt based Fischer-Tropsch catalyst, the catalyst including a porous catalyst support and metallic cobalt crystallites within the support, and the catalyst having i. a proportion of its cobalt in reducible form, with this proportion being expressible as $\Omega$ mass %, based on the total pre-reduced catalyst mass;
 ii. when freshly reduced, a mono-modal Gaussian metallic cobalt crystallite size distribution;
 iii. when freshly reduced, a metallic cobalt surface area, in $m^2$ per gram of catalyst, of from 0.14 $\Omega$ to 1.03 $\Omega$; and
 iv. when freshly reduced, a catalyst geometry that ensures a stabilized Fischer-Tropsch synthesis effectiveness factor of 0.9 or greater.

It was surprisingly found that the cobalt based catalyst of the first aspect of the invention displayed enhanced initial and stabilized intrinsic Fischer-Tropsch activity.

By 'stabilized Fischer-Tropsch synthesis effectiveness factor' is meant the effectiveness factor of the stabilized catalyst. A stabilized cobalt based Fischer-Tropsch catalyst is defined as a catalyst that has been conditioned completely during slurry phase Fischer-Tropsch synthesis at realistic Fischer-Tropsch synthesis conditions using an ultra pure synthesis gas, ie a synthesis gas that contains no contaminant compounds other than $H_2$ and CO that could affect catalytic deactivation.

By 'realistic Fischer-Tropsch synthesis conditions' is meant reaction conditions of 225±5° C. and 20 bar, and % ($H_2$+CO) conversion of 60±10% using a feed gas comprising about 50 vol % $H_2$, about 25 vol % CO, and with the balance being Ar, $N_2$, $CH_4$ and/or $CO_2$.

By 'freshly reduced' is meant a catalyst that has been activated without subjecting such a catalyst to Fischer-Tropsch synthesis.

In this specification, unless explicitly otherwise stated, where reference is made to catalyst mass, the mass given pertains to the calcined catalyst mass or pre-reduced catalyst mass, ie the catalyst mass before any reduction of the catalyst is effected.

Preferably, the metallic cobalt surface area of the catalyst, when freshly reduced, may be, in $m^2$ per gram of catalyst, from 0.28 $\Omega$ to 0.89 $\Omega$.

The sizes of a majority of the cobalt crystallites may be greater than 8 nm.

It was surprisingly found that the supported cobalt catalysts of the present invention with their large cobalt crystallites, ie with the majority of metallic cobalt crystallite sizes greater than 8 nm and thus relatively low cobalt metal areas, were not severely affected by oxidation. With these catalysts, while their time zero (ie at the start of a run) intrinsic activities, when used for Fischer-Tropsch synthesis, may be lower than those of supported cobalt catalysts having smaller cobalt crystallites (i.e. having the majority of cobalt crystallite sizes smaller than 8 nm), superior or enhanced initial and stabilized intrinsic activities were surprisingly obtained since there was much less deactivation with the novel catalysts than with supported cobalt catalysts having the majority metallic cobalt crystallite sizes smaller than, or equal to, 8 nm.

The porous catalyst support may be a calcined support. Thus, the supported cobalt catalyst of the first aspect of the invention may be that obtained by impregnating a porous catalyst support with cobalt or a cobalt precursor, particularly cobalt nitrate, calcining the impregnated support to obtain a cobalt catalyst precursor; and reducing the catalyst precursor to obtain the supported cobalt catalyst.

The catalyst support may be a modified catalyst support. The modified catalyst support may comprise catalyst support particles coated with a modifying agent, which may be carbon or one or more metals of Group IA and/or Group IIA of the Periodic Table of Elements, ie one of more metals selected from Li, Na, K, Rb, Cs, Fr, Be, Mg, Ca, St, Ba, Ra and mixtures thereof. It was found that the catalyst had a surprisingly large increase in initial intrinsic activity when used for Fischer-Tropsch synthesis, and hence a surprisingly high stabilized intrinsic activity, when a modified catalyst support was used, particularly when a carbon or barium coated support was used.

When barium is used to coat the support, the maximum amount of barium that can be used is determined by the influence of the barium on the pore volume of the support as well as on the solubility of the barium precursor. The pore volume of the support should be large enough to accommodate the required amount of cobalt nitrate to be able to obtain a supported cobalt catalyst with the required cobalt loading. The solubility of the barium precursor should be large enough to be able to add the barium precursor in one impregnation step to the support. In practice the maximum amount of barium may be 10% by mass, based on the catalyst mass. The minimum amount of barium is determined by the minimum amount of barium that is effective in increasing the stabilized intrinsic Fischer-Tropsch activity of the cobalt catalysts, and may be 0.2% by mass.

When carbon is used to coat the support, the maximum amount of carbon that can be used as an effective coating is determined by the influence of the carbon coating on the pore volume of the original catalyst support, as the pore volume of the catalyst support determines how much cobalt can be impregnated into the catalyst support. This is particularly important when a catalyst with a relatively high cobalt loading is required. Similarly, the minimum amount of carbon that can be used as an effective coating is determined by the minimum level of carbon that still provides the required positive effect on the stabilized intrinsic Fischer-Tropsch synthesis performance of the cobalt catalyst. Thus, the maximum level of carbon may be 40 g C/100 g support, preferably 20 g C/100 g support, and more preferably 10 g C/100 g support, while the minimum level of carbon may be 0.1 g C/100 g support, preferably 0.5 g C/100 g support, and more preferably 1.2 g C/100 g support.

In principle, the coating of the catalyst support particles can be effected by any suitable method. For example, the carbon coated catalyst support may be prepared by coating pre-shaped spherical porous catalyst support particles with a uniform carbon based layer in accordance with the method as described in EP 0681868, which is hence incorporated herein by reference.

According to a second aspect of the invention, there is provided a cobalt based catalyst precursor, which includes a porous catalyst support and cobalt oxide crystallites within the support, the precursor having a proportion of its cobalt in reducible form, with this proportion being expressible as $\Omega$ mass %, based on the total precursor mass, and with the precursor being capable of yielding, on fresh reduction thereof, a catalyst having a mono-modal Gaussian metallic cobalt crystallite size distribution; a metallic cobalt surface area, in $m^2$ per gram of catalyst, of from 0.14 $\Omega$ to 1.03 $\Omega$; and a catalyst geometry that ensures a stabilized Fischer-Tropsch synthesis effectiveness factor of 0.9 or greater.

The porous catalyst support of the precursor may be the same as that of the catalyst of the first aspect of the invention, and may thus be a modified catalyst support as hereinbefore described.

According to a third aspect of the invention, there is provided a process for preparing a cobalt based catalyst precursor, which process comprises in a support impregnation stage, impregnating a particulate porous modified catalyst support with a cobalt salt, and partially drying the impregnated support, to obtain a partially dried impregnated support; and in a calcination stage, calcining the partially dried impregnated support to obtain the cobalt based catalyst precursor, with the precursor comprising calcined porous modified catalyst support particles containing cobalt oxide crystallites, and the precursor having a proportion of its cobalt in reducible form, with this proportion being expressible as $\Omega$ mass %, based on the total precursor mass, and with the precursor being capable of yielding, on fresh reduction thereof, a catalyst having a mono-modal Gaussian metallic cobalt crystallite size distribution; a metallic cobalt surface area, in $m^2$ per gram of catalyst, of from 0.14 $\Omega$ to 1.03 $\Omega$; and a catalyst geometry that ensures a stabilized Fischer-Tropsch synthesis effectiveness factor of 0.9 or greater.

The resultant cobalt catalyst precursor will thus, in practice, be reduced to obtain the cobalt catalyst, which will thus have the enhanced or superior initial as well as stabilized intrinsic activity.

According to a fourth aspect of the invention, there is provided a process for preparing a cobalt based Fischer-Tropsch catalyst, which process comprises in a support impregnation stage, impregnating a particulate porous modified catalyst support with a cobalt salt, and partially drying the impregnated support, to obtain a partially dried impregnated support;

in a calcination stage, calcining the partially dried impregnated support to obtain a cobalt based catalyst precursor, with the precursor comprising calcined porous modified catalyst support particles containing cobalt oxide crystallites; and in a reduction stage, reducing the cobalt catalyst precursor, to obtain a cobalt based catalyst which has (i) a proportion of its cobalt in reducible form, with this proportion being expressible as $\Omega$ mass %, based on the total pre-reduced catalyst mass; (ii) when freshly reduced, a mono-modal Gaussian metallic cobalt crystallite size distribution; (iii) when freshly reduced, a metallic cobalt surface area, in $m^2$ per gram of catalyst, of from 0.14 $\Omega$ to 1.03 $\Omega$; and (iv) when freshly reduced, a catalyst geometry that ensures a stabilized Fischer-Tropsch synthesis effectiveness factor of 0.9 or greater.

The cobalt salt may, in particular, be cobalt nitrate, $Co(NO_3)_2 \cdot 6H_2O$.

The modified catalyst support may be any commercially available porous oxidic catalyst support, such as alumina ($Al_2O_3$), silica ($SiO_2$), a silica-alumina ($SiO_2$—$Al_2O_3$), titania ($TiO_2$) and magnesia (MgO), coated with carbon or one or more metals of Group IA and/or Group II of the Periodic Table of Elements as a modifying agent, as hereinbefore described.

The support may be a protected modified catalyst support, containing, for example, silicon as a modifying component, as described in WO 99/42214 and which is hence incorporated herein by reference.

The processes according to the third and fourth aspects may, if necessary, include preparing the modified support, ie they may include modifying the support particles by coating them with the modifying agent.

The support impregnation may, in principle, be effected by any known impregnation method, eg incipient wetness impregnation, or slurry phase impregnation. Similarly, the calcination may be performed in any known calcination unit, eg fluidized bed, fixed bed, furnace, rotary kiln, and/or torbed calciner, preferably at temperatures between 150° C. and 400° C., more preferably between 200° C. and 300° C. In particular, the calcination may be in accordance with that described in U.S. 60/168,604, and which is thus incorporated herein by reference. The calcination may thus involve fluidized bed calcination as described in U.S. 60/168,604.

The cobalt based catalyst precursor may be obtained by a 2-step slurry phase impregnation, drying and calcination process. The 2-step process includes, in a first step, impregnating the catalyst support with the cobalt salt, partially drying the impregnated support, and calcining the partially dried support, to obtain a calcined material, and thereafter, in a second step, impregnating the calcined material with the cobalt salt, partially drying the impregnated material, and calcining the partially dried material, to obtain the catalyst precursor.

The process may include partially reducing the calcined material prior to impregnating it with the cobalt salt. The partial reduction of the calcined material may be effected at a temperature of 100° C. to 300° C., more preferably at a temperature of 130° C. to 250° C. The partial reduction of the calcined material may be effected by contacting the calcined material with a hydrogen and/or carbon monoxide containing gas as a reducing gas.

According to a fifth aspect of the invention, there is provided a process for preparing a cobalt catalyst precursor, which process comprises in a first step, in a support impregnation stage, impregnating a particulate porous catalyst support with a cobalt salt, and partially drying the impregnated support, and, in a calcination stage, calcining the partially dried impregnated support, to obtain a calcined material;

at least partially reducing the calcined material; and thereafter in a second step, in a support impregnation stage, impregnating the at least partially reduced material with a cobalt salt, and partially drying the impregnated material, and, in a calcination stage, calcining the partially dried impregnated material, to obtain the cobalt catalyst precursor, with the precursor comprising the calcined porous catalyst support with cobalt oxide crystallites present therein, and having a proportion of its cobalt in reducible form, with this proportion being expressible as $\Omega$ mass %, based on the total precursor mass, and with the precursor being capable of yielding, on fresh reduction thereof, a catalyst having a mono-modal Gaussian metallic cobalt crystallite size distribution; a metallic cobalt surface area, in $m^2$ per gram of catalyst, of from 0.14 $\Omega$ to 1.03 $\Omega$; and a catalyst geometry that ensures a stabilized Fischer-Tropsch synthesis effectiveness factor of 0.9 or greater.

As discussed hereinbefore, the resultant cobalt catalyst precursor will thus, in practice, be reduced to obtain the cobalt catalyst, which will thus have the enhanced or superior initial as well as stabilized intrinsic activity.

Thus, according to a sixth aspect of the invention, there is provided a process for preparing a cobalt catalyst, which process comprises in a first step, in a support impregnation stage, impregnating a particulate porous catalyst support with a cobalt salt, and partially drying the impregnated support, and, in a calcination stage, calcining the partially dried impregnated support, to obtain a calcined material;

at least partially reducing the calcined material;

in a second step, in a support impregnation stage, impregnating the at least partially reduced material with a cobalt salt, and partially drying the impregnated material, and, in a calcination stage, calcining the partially dried impregnated material, to obtain the cobalt catalyst precursor, with the precursor comprising the calcined porous catalyst support with cobalt oxide crystallites present therein, and having a proportion of its cobalt in reducible form, with this proportion being expressible as $\Omega$ mass %, based on the total precursor mass, and with the precursor being capable of yielding, on fresh reduction thereof, a catalyst having a mono-modal Gaussian metallic cobalt crystallite size distribution; a metallic cobalt surface area from 0.14 $\Omega$ $m^2$ to 1.03 $\Omega$ $m^2$, per gram of catalyst; and a catalyst geometry that ensures a stabilized Fischer-Tropsch synthesis effectiveness factor of 0.9 or greater; and in a reduction stage, reducing the cobalt catalyst precursor, to obtain the supported cobalt catalyst which (i) has a proportion of its cobalt in reducible form, with this proportion being expressible as $\Omega$ mass %, based on the total pre-reduced catalyst mass; (ii) has, when freshly reduced, a mono-modal Gaussian metallic cobalt crystallite size distribution; (iii) has, when freshly reduced, a metallic cobalt surface area, in $m^2$ per gram of catalyst, of from 0.14 $\Omega$ to 1.03 $\Omega$; and (iv) has, when freshly reduced, a catalyst geometry that ensures a stabilized Fischer-Tropsch synthesis effectiveness factor of 0.9 or greater.

The catalyst support may be a modified catalyst support, as hereinbefore described. The support may even be a protected modified catalyst support, as hereinbefore described. The processes according to the fifth and sixth aspects may, if necessary, include preparing the modified support.

The cobalt salt may, in the processes of the fifth and sixth aspects, be cobalt nitrate.

The support impregnation, drying and calcination may, in particular, be in accordance with the process described in our copending WO 00/20116, which is thus incorporated herein by reference. The precursor preparation may thus involve a 2-step slurry phase impregnation, drying and calcination process as described in WO 00/20116, which is dependant on a desired active component loading requirement and the pore volume of the porous oxidic catalyst support.

The support impregnation and drying may typically be effected in a conical vacuum drier with a rotating screw or in a tumbling vacuum drier.

The catalyst precursor may contain between 5 g Co/100 g support and 70 g Co/100 g support, preferably between 20 g Co/100 g support and 50 g Co/100 g support.

During either of the two slurry phase impregnation steps, a water soluble precursor salt of palladium (Pd) or platinum (Pt) or a mixture of such salts may be added, as a dopant capable of enhancing the reducibility of the cobalt. Preferably, the dopant is added in a mass proportion of the palladium metal, the platinum metal or the mixture of palladium and platinum metals to the cobalt metal of between 0.01:100 to 0.3:100.

The invention extends also to a cobalt catalyst, when produced by the process of the fourth or sixth aspect of the invention, and to a cobalt catalyst precursor, when produced by the process of the third or fifth aspect of the invention.

According to a seventh aspect of the invention, there is provided a process for producing hydrocarbons, which includes contacting synthesis gas comprising hydrogen ($H_2$) and carbon monoxide (CO) at an elevated temperature between 180° C. and 250° C. and an elevated pressure between 10 and 40 bar with a cobalt catalyst according to the invention, in a slurry phase Fischer-Tropsch reaction of the hydrogen with the carbon monoxide, to obtain hydrocarbons.

The invention extends also to hydrocarbons when produced by the process as hereinbefore described.

The invention will now be described in more detail with reference to the following non-limiting examples and with reference to the drawings.

BRIEF DESCRIPTION OF THE DRAWINGS

In the drawings,

FIG. 3 shows a superimposition of the Relative Intrinsic Activity Factor (R.I.A.F.) profiles of 5 selected micro slurry phase CSTR Fischer-Tropsch synthesis runs on catalyst B;

FIG. 5 is a proposed bi-modal Gaussian probability distribution of the metallic cobalt content of a freshly reduced sample of catalyst B;

FIG. 6 is an illustration of the postulated influence of oxidation as deactivation mechanism during slurry phase Fischer-Tropsch operation under realistic synthesis conditions as applied to catalyst B;

DETAILED DESCRIPTION OF PREFERRED EMBODIMENTS

EXAMPLE 1

Figure 1:
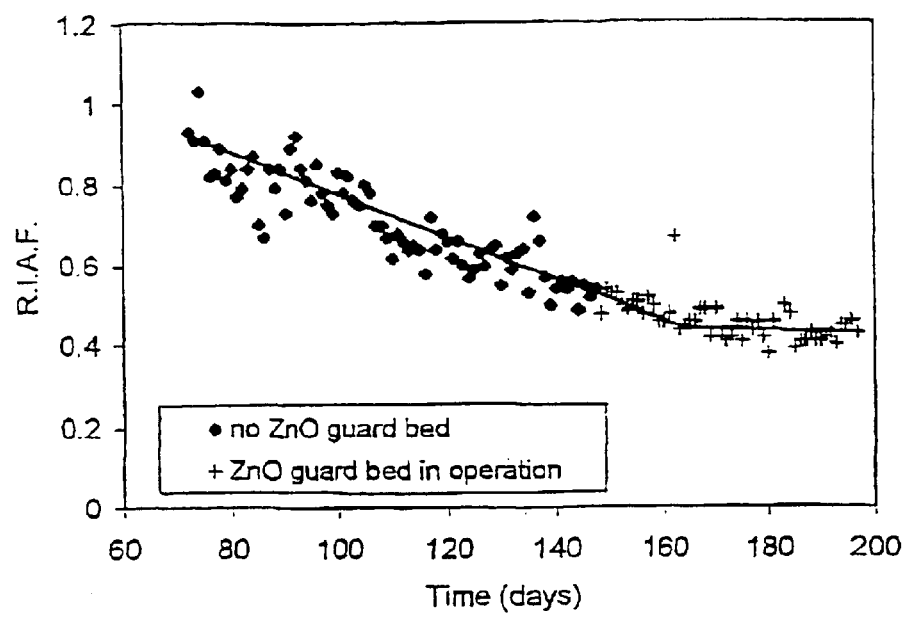
FIG. 1 shows the deactivation behaviour of catalyst B during a Fischer-Tropsch synthesis demonstration run, and the effect of the introduction of a ZnO guard bed in the APG feed on the deactivation behaviour.

Catalyst B (30 g Co/100 g $Al_2O_3$) (not in Accordance with the Invention)

1.1 Preparation

A Pt promoted catalyst was prepared on SASOL Germany GmbH's trademark product: Puralox SCCa 5/150, as a selected pre-shaped $Al_2O_3$ support, in accordance with the method of aqueous slurry phase impregnation and vacuum drying, followed by direct fluidized bed calcination, in accordance with Catalyst Example 1 of WO 00/20116, or one of Catalysts D, E, G or H of U.S. 60/168,604.

In preparation for laboratory scale slurry phase continuous stirred tank reactor ('CSTR') Fischer-Tropsch synthesis runs, this calcined material was reduced and wax coated in accordance with the following procedure:

27.5 g of the catalyst was reduced at 1 bar pure $H_2$ (space velocity $\geq$ 200 $ml_n$ $H_2$/g catalyst/h) whilst the temperature was increased from 25° C. to 380° C.–425° C. at a rate of 1° C./min whereafter the temperature was kept constant at this temperature of 380° C.–425° C. for 16 hours.

The reduced catalyst was allowed to cool down to room temperature at which stage the hydrogen was replaced by argon, and the catalyst unloaded in molten Fischer-Tropsch wax under the protection of an argon blanket. This wax coated catalyst was then transferred to the slurry reactor.

The following characteristics apply to the catalyst: a catalyst sample comprising 30 g Co and 100 g $Al_2O_3$, has a calcined mass (before any reduction) of 153.8 g and a freshly reduced mass of 133.8 g.

1.2 CSTR Fischer-Tropsch Synthesis Run

An extended slurry phase CSTR Fischer-Tropsch synthesis run (number 106F) was performed on catalyst B. This run lasted about ('ca') 90 days, during which the following synthesis conditions were maintained:

| | |
|---|---|
| Reactor temperature | 220.5° C. |
| Reactor pressure | 20.3 bar |
| Catalyst inventory | 20.8 g |
| ($H_2$ + CO) space velocity | 2169 $ml_n$/(g catalyst.h) |
| APG space velocity | 2452 $ml_n$/(g catalyst.h), | where 'APG' is an acronym for Arge Pure Gas, ie the commercial synthesis gas produced at Schümann-Sasol (Pty) Limited in Sasolburg, South Africa, according to the method of coal gasification, followed by Rectisol (trademark) purification.

| Feed gas composition: | |
|---|---|
| $H_2$ | 49.1 vol % |
| CO | 25.9 vol % |
| $CH_4$ | 9.3 vol % |
| $CO_2$ | 0.5 vol % |
| Ar | 15.2 vol % |

An evaluation of the observed synthesis performance data of this run (ie 106F) resulted in the following conclusions:

an initial R.I.A.F. of 2.6, viz: $a_i$=2.6 an intrinsic activity profile (ex $t_i$ where t=time) that could be broken up into three phases, distinguishable by 2 break-points.

Relative (Fischer-Tropsch) Intrinsic Activity Factor ('R.I.A.F.') is defined as follows:

Consider an arbitrary slurry phase cobalt Fischer-Tropsch catalyst, displaying the following observed synthesis performance in a CSTR:

$r_{FT}$=Z moles CO converted to Fischer-Tropsch products per gram catalyst per second, observed at T=y Kelvin, at the following set of reactor partial pressures:

$P_{H2}$=v bar $P_{co}$=$\tau$ bar then the definition of R.I.A.F. is as follows:

R.I.A.F=$[Z(1+1.82\tau)^2]/[49480.9e^{(-11113.4/y)}v\tau]$

Initial intrinsic Fischer-Tropsch activity ($a_i$) of a slurry phase cobalt based catalyst is defined as follows:

$a_i$=the R.I.A.F. after 15 hours on stream (ie $t_i$=time initial) of continuous exposure to the following set of gradientless slurry phase synthesis conditions:

220° C., 20 bar, %($H_2$+CO) conversion in excess of 50%, obtained with a feed gas of composition: ca 50 vol % $H_2$ and ca 25 vol % CO, the balance consisting of Ar, $N_2$, $CH_4$ and/or $CO_2$.

As a result of this observation, it is postulated that a total of 4 deactivation phases (ie phases I, II, III and IV) fully describe the intrinsic activity profile of catalyst B during extended slurry phase Fischer-Tropsch synthesis runs under realistic conditions.

1.2.1 Phase IV Deactivation—Portion of a Run Longer than 40 to 60 Days After Commencement, Under Realistic Slurry Phase Fischer-Tropsch Synthesis Conditions This deactivation is a continuous and irreversible process.

Sulphur poisoning is the dominating mechanism during phase IV deactivation.

The correlation between the Fischer-Tropsch catalyst active site density and the R.I.A.F. is as follows:

Consider a well conditioned cobalt catalyst operating in a slurry CSTR, ie low level sulphur poisoning being solely responsible for catalyst deactivation.

Assumptions:
   the sulphur containing compounds present in the pure synthesis gas are all mono-atomic with respect to sulphur
   the poisoning ratio is one sulphur atom per single active site
   the sulphur absorption is quantitative and occurs selectively on metallic cobalt Nomenclature:

$\alpha$=observed linear deactivation rate of a well conditioned cobalt catalyst expressed in terms of R.I.A.F. units lost per hour $\beta$=sulphur content of pure synthesis gas expressed in terms of volume parts per billion X=pure synthesis gas feed rate expressed in terms of $m^3{}_n$ per kg catalyst per hour Thus, (X$\beta$ 4.459×10$^{-8}$) mole S is introduced to the CSTR per kg catalyst per hour. Therefore, a R.I.A.F. of a corresponds to an active site density of (X$\beta$ 4.459×10$^{-8}$) mole per kg catalyst. A single R.I.A.F. unit corresponds to [(X$\beta$ 4.459×10$^{-11}$)/$\alpha$] mole sites/g catalyst.

During Fischer-Tropsch synthesis demonstration run WPP54 an APG feed was used that was not cleaned by passing through absorbents, and substantial phase IV deactivation was observed (FIG. 1). After introducing a ZnO sulphur guard bed the intrinsic Fischer-Tropsch synthesis activity levelled off, indicating that the observed deactivation, prior to the introduction of the ZnO bed, was mainly due to sulphur.

Figure 2:
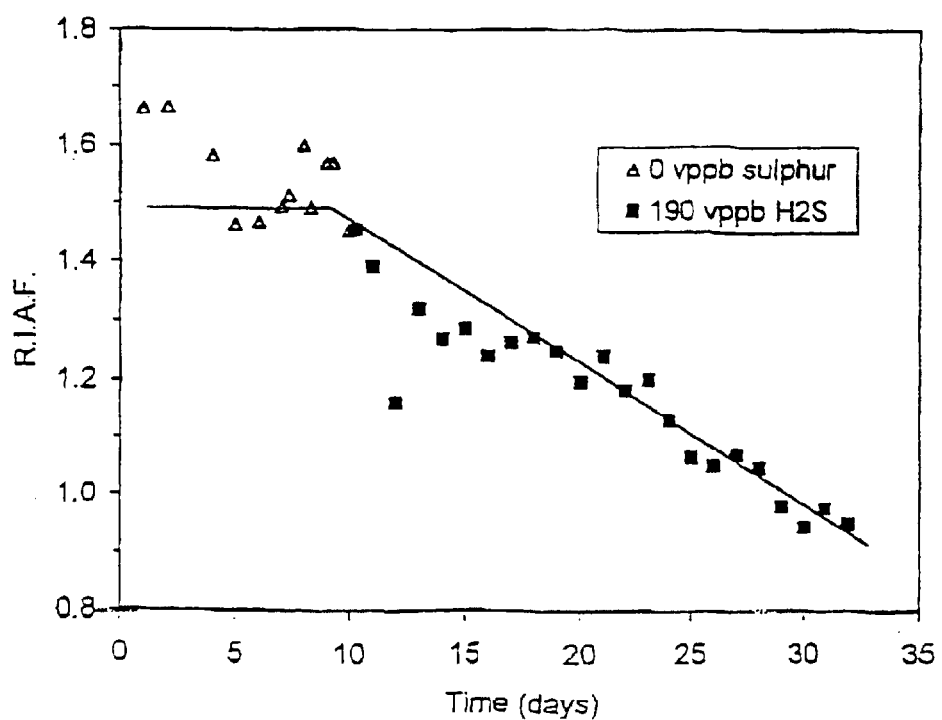
FIG. 2 shows the deactivation rate of catalyst B in a laboratory micro CSTR Fischer-Tropsch synthesis run, due to the introduction of $H_2S$ at a level of 190 vppb and a space velocity of 2.22 $m^3_n$/(kg catalyst.h)

A conditioned catalyst sample was taken, after about 120 days on line, ie after levelling off and thus properly conditioned, from a Fischer-Tropsch synthesis demonstration run, which was performed using a synthesis gas feed that was passed trough a ZnO sulphur guard bed. This catalyst sample was tested in a laboratory micro CSTR for deactivation behaviour by introducing a known amount of H$_2$S during this Fischer-Tropsch synthesis run, by means of a permeation tube system (FIG. 2). A phase IV deactivation rate of 1.09×10$^{-3}$ R.I.A.F. units/hour was observed with a gas (containing 190 vppb H$_2$S) space velocity of 2.22 $m^3{}_n$/(kg catalyst.h). An application of the above-mentioned correlation to this information, implies that a single R.I.A.F. unit corresponds to 1.72×10$^{-5}$ mole sites/g catalyst.

1.2.2 Phase III Deactivation—Portion of a Run from About 5 Days up to 40–60 Days After Commencement, Under Realistic Slurry Phase Fischer-Tropsch Synthesis Conditions Contributing to this deactivation phase is sulphur poisoning in accordance with 1.2.1. In addition to this deactivation mechanism, slow oxidation of metallic cobalt crystallites, smaller than a threshold size, also takes place. This particular deactivation mechanism is described as: ex $t_i$ oxidation.

The 'threshold size' is defined as the maximum crystallite diameter of the whole set of cobalt metal crystallites that will oxidize when exposed to a realistic Fischer-Tropsch synthesis environment.

It is further assumed that the metallic cobalt crystallites, in the case of reduced supported cobalt catalysts, are hemispherical, thus implying that
   the surface area of a single crystallite=$(\pi x^2)/2$
   the volume of a single crystallite=$0.083\pi x^3$
where x=the diameter of the postulated hemispherical crystallites, and also referred to as the crystallite size Although the oxidation of bulk phase metallic cobalt to either CoO or Co$_3$O$_4$, under typical Fischer-Tropsch synthesis conditions, is unlikely from a thermodynamic point of view, strong literature support does, however, exist in favour of cobalt catalyst oxidation during Fischer-Tropsch synthesis.

In the case of catalyst B, the following characteristic deactivation parameters can be assumed during slurry phase Fischer-Tropsch synthesis conditions:

TABLE 1

| Temperature (° C.) | Extent of ex $t_i$ oxidation (% drop in $a_i$) | Deactivation rate associated with ex $t_i$ oxidation (R.I.A.F. units/day) |
|---|---|---|
| 220 | 15 | 1.0 × 10$^{-2}$ |

1.2.3 Phase II Deactivation—Portion of a Run from Time Initial ('$t_i$') up to About 5 Days After Commencement, Under Realistic Slurry Phase Fischer-Tropsch Synthesis Conditions Contributing to this deactivation phase, are:
   sulphur poisoning in accordance with 1.2.1
   ex $t_i$ oxidation in accordance with 1.2.2

In addition to these two deactivation mechanisms, it is believed that rejuvenatable poisoning also takes place. By "rejuvenatable poisoning" is understood that recovery can be effected through an in-situ pure hydrogen treatment step at 20 bar and 220° C., ie normal Fischer-Tropsch synthesis conditions. The following two published deactivation mechanisms could take place:
   the screening off of active sites by carbonaceous residues lie fouling), removable through hydrolysis. With this mechanism, a pure hydrogen treatment step should restore initial Fischer-Tropsch synthesis rates, and this will be facilitated by the presence of ruthenium as a promoter, thus exploiting its known strong hydrogenolysis characteristic. The option of regeneratingdeactivated catalysts by a hydrogen treatment step can be problematic on supported mono-metallic cobalt, ie in the absence of Ru, Fischer-Tropsch catalysts.
   rejuvenatable poisoning of supported cobalt Fischer-Tropsch catalysts through contaminants, other than sulphur containing compounds, eg NH$_3$ and/or HCN, present in the synthesis gas.

This theory of rejuvenatable poisoning, lasting for ca 5 days under the influence of realistic slurry phase CSTR Fischer-Tropsch synthesis conditions, was tested during synthesis run numbers 35F, 41F, 215F, 317$ and 319$.

The Fischer-Tropsch synthesis run number 41F was performed on Catalyst B. This run was performed under a set of realistic slurry phase CSTR conditions, and was subjected to the following two in-situ pure hydrogen treatment steps:

H$_2$ Treatment Number A:

At period 178.3 hours on stream, the feed gas (ie APG spiked with 15 vol % Ar), was replaced with pure hydrogen (feed rate of 0.5 dm$^3{}_n$/min) at a reactor pressure of 20 bar and a reactor temperature of 220° C. This pure H$_2$ treatment step was maintained for 10.2 hours, after which the pure hydrogen was replaced with the same synthesis gas (ie APG spiked with 15 vol % Ar). The first Fischer-Tropsch synthesis performance analysis (ex H$_2$ treatment number A) occurred 1.8 hours after the re-introduction of synthesis gas.

H$_2$ Treatment Number B:

At period 471.1 hours on stream, the feed gas (ie APG spiked with 15 vol % Ar) was again replaced with pure hydrogen (feed rate of 0.5 dm$^3{}_n$/min) at a reactor pressure of 20 bar and a reactor temperature of 220° C. This pure hydrogen treatment step was maintained for 39 hours, after which the pure hydrogen was replaced with the same synthesis gas (ie APG spiked with 15 vol % Ar). The first Fischer-Tropsch synthesis performance analysis (ex $H_2$ treatment B) occurred 2.0 hours after the re-introduction of synthesis gas.

An evaluation of the observed synthesis performance data of run number 41F resulted in the following observations/conclusions:

The intrinsic activity behaviour of catalyst B, ex $H_2$ treatment numbers A and B, displayed similarities with that of phase II deactivation (ie ex $t_i$). On the basis that this agreement is accepted, it is concluded that rejuvenatable poisoning contributed significantly during the phase II deactivation as observed during synthesis run number 41F; and An extrapolation of the results obtained provided a R.I.A.F. of 3.0 at time zero. It is thus concluded that the extrapolated R.I.A.F. at time zero, that corrects for any deactivation caused by phases II, III and IV, is equal to 3.0.

It is known from the literature that catalyst rejuvenation can also be effected through an inert gas treatment step at typical Fischer-Tropsch synthesis conditions (ie 220° C. and 20 bar). It thus appeared as if the presence of hydrogen during the in-situ rejuvenation of catalyst B was not necessary, and that a pure stripping step sufficed, perhaps having offered an incentive for considering $Al_2O_3$ support materials with a larger pore diameter than the 12 nm of the preferred Sasol Germany GmbH $Al_2O_3$: Puralox SCCa 5/150. This premise of an in-situ inert gas rejuvenation step was followed-up, but could not be repeated. It was thus concluded that the presence of hydrogen is imperative during catalyst rejuvenation, which is in line with published observations and supports the viewpoint that catalyst fouling may not be the rejuvenatable poisoning mechanism of choice.

Referring to FIG. 3, an evaluation of the observed synthesis performance data of synthesis run numbers 29F, 106F, 215F, 317$ and 319$, ie synthesis runs performed on catalyst B at realistic slurry phase Fischer-Tropsch synthesis conditions, resulted in the following observations/conclusions:

Rejuvenatable poisoning was not always observed, and was dependent on particular time slots. The behaviour displayed during synthesis run numbers 29F and 106F could be regarded as typical of all extended slurry micro CSTR Fischer-Tropsch runs performed over a lengthy period, having utilized APG as synthesis gas. Synthesis run numbers 317$, 319$ and 215F were performed over a subsequent much shorter period, also with APG as synthesis gas. It was concluded that rejuvenatable poisoning, present during phase II deactivation, is not to be associated with the mechanism of active site fouling by high molecular weight hydrocarbons. The mechanism of rejuvenatable poisoning by feed gas containing contaminants, eg $NH_3$ and/or HCN, is therefore preferred; and If it is assumed that rejuvenatable phase II poisoning was completely absent during synthesis run numbers 317$, 319$ and 215F, an extrapolated time zero R.I.A.F. of 2.9 was obtained from the results. This extrapolated time zero R.I.A.F. of 2.9 supports the value of 3.0 referred to hereinbefore, ie the extrapolated R.I.A.F. at time zero that corrects for any deactivation caused by phase II, III and IV deactivations.

1.2.4 Phase I Deactivation—Portion of a Slurry Phase Fischer-Tropsch Run up to Time Initial (ie $t_i$)

Contributing to this deactivation phase, are:

Sulphur poisoning in accordance with 1.2.1 (ie phase IV)

Ex $t_i$ oxidation in accordance with 1.2.2 (ie phase III deactivation)

Rejuvenatable poisoning in accordance with 1.2.3 (ie phase II deactivation)

If an extrapolated correction for all three of these deactivation mechanisms is made in the case of the synthesis performance of catalyst B, under the influence of a realistic set of Fischer-Tropsch synthesis conditions, a time zero R.I.A.F. of 3.0 was derived. However, as set out hereinbefore in 1.2.1, a single R.I.A.F. unit corresponds to $1.72 \times 10^{-5}$ mole sites/g catalyst. Thus, a time zero active site density of $5.16 \times 10^{-5}$ mole surface metallic cobalt atoms per gram of catalyst B would account for the complete influence of phases II, III and IV deactivation in the case of a realistic CSTR synthesis environment.

If it is assumed that a single surface metallic cobalt atom occupies $0.0662$ $nm^2$, an active site density of $5.16 \times 10^{-5}$ mole Fischer-Tropsch sites per gram of catalyst would correspond to a cobalt metal surface area of $2.06$ $m^2/gram$ catalyst. Thus, a time zero cobalt metal surface area of ca $2.1$ $m^2$ per gram of catalyst B would account for the complete influence of phases II, III and IV deactivation in the case of a realistic CSTR synthesis environment.

However, an interpretation of $H_2$ chemisorption analyses performed on freshly reduced samples of catalyst B resulted in the conclusion that the cobalt metal surface area of freshly reduced lie time zero) catalyst B=11.9 $m^2/g$ catalyst Phase I deactivation of Catalyst B is associated with significant catalyst induction (i.e. in addition to the three hypothesized deactivation mechanisms associated with deactivation phases: II, III and IV), that amounted to a loss of $11.9-2.1=9.8$ $m^2$ cobalt metal surface area per gram catalyst. On the basis of published Mössbauer Emission Spectroscopy ('MES') and Temperature Gravimetric Analysis ('TGA') studies, the mechanism of almost instantaneous oxidation of metallic cobalt crystallites which are significantly smaller than a threshold size, is hypothesized. This catalyst oxidation is thus distinguished from the previously postulated: ex $t_i$ oxidation, and is referred to as: pre $t_i$ oxidation.

The overall impact of this pre $t_i$ oxidation on catalyst B was estimated as follows: The metallic cobalt surface area of the freshly reduced catalyst=11.9 $m^2/g$ catalyst. However, a single surface metallic cobalt atom occupies $0.0662$ $nm^2$. Thus, freshly reduced catalyst B contains $2.98 \times 10^{-4}$ mole Fischer-Tropsch active sites per gram catalyst. However, a single R.I.A.F. unit corresponds to $1.72 \times 10^{-5}$ mole sites per gram catalyst, as set out in 1.2.1. Thus, the R.I.A.F. of freshly reduced catalyst B (ie R.I.A.F. at time zero)=17.3. Therefore, pre $t_i$ oxidation is exclusively responsible for the loss of $17.3-3.0=14.3$ R.I.A.F. units in the case of catalyst B, ie corresponding to. a loss of 9.8 $m^2$ cobalt metal surface area per gram of catalyst.

1.3 Description of the Metallic Cobalt Crystallite Size Distribution of a Freshly Reduced Catalyst B Sample 1.3.1 Known Characteristics of Catalyst B From $H_2$ chemisorption analyses of freshly reduced samples of catalyst B, the following conclusions were arrived at:

Metallic cobalt surface area=11.9 $m^2/g$ catalyst

Metallic cobalt crystallite size of maximum abundance=6 nm, a value that was also qualitatively confirmed through the application of High Resolution Transmission Electron Microscopy ('HRTEM')

The value of 6 nm, as the metallic cobalt crystallite size of maximum abundance in the case of the freshly reduced catalyst B sample, was also confirmed during the application of the magnetic method. From this work it was also estimated that 30 mass % of the total metallic cobalt content of the freshly reduced catalyst B sample, is contained in crystallites larger than 15 nm.

The following set of known characteristics must therefore be simultaneously answered by any model that is to be considered as a feasible description of the metallic cobalt crystallite size distribution for a freshly reduced catalyst B sample.

Metallic cobalt crystallite size of maximum abundance=6 nm

Metallic cobalt surface area=11.9 $m^2/g$ catalyst

Mass % of the total metallic cobalt content contained in crystallites larger than 15 nm=30

1.3.2 Model Selection for the Description of the Metallic Cobalt Crystallite Size Distribution of the Freshly Reduced Sample of Catalyst B The following list of standard probability distributions were considered in order to identify a feasible Crystallite Size Distribution ('CSD') model, i.e. feasibility implies compliance with 1.3.1.

a) Mono-modal chi-square distribution
b) F-distribution
c) Mono-modal Gaussian distribution
d) Mono-modal asymmetrical normal distribution
e) Bi-modal Gaussian distribution An evaluation of options a)–d) resulted in the conclusion that it was impossible to satisfy all three characteristics of 1.3.1 simultaneously by means of a mono-modal crystallite size probability distribution.

Option e), ie a bi-modal Gaussian probability distribution, was found to be viable, and can be described by the following mathematical equation:

$$f_{\mu_1,\mu_2,\sigma_1,\sigma_2}(x)=[\beta g_{\mu_1,\sigma_1}(x)+(1-\beta)g_{\mu_2,\sigma_2}(x)] \quad (1)$$

where:
i) $f_{\mu_1,\mu_2,\sigma_1,\sigma_2}(x)$=the crystallite population with a crystallite size of x nm ii) $g_{\mu_1,\sigma_1}(x)=(1/(\sigma_i\sqrt{2\pi}))e^{[-x-\mu_i)^2/(2\sigma_i 2)]}$ (2)

iii) $0 \leq \beta \leq 1$ iv) $0 \leq \sigma_i \leq (\mu_i/2.67)^*$, and $\mu_i > 0$ (3)

*Note:

$$\int_{-\infty}^{0} f_{\mu_1,\mu_2,\sigma_1,\sigma_2}(x)dx > 0$$

is undesired from a physical point of view (i.e. crystallites with a negative diameter). In order to accommodate this situation, a restriction was placed on the maximum attainable (i.e. negligible) value of:

$$\int_{-\infty}^{0} g_{\mu_1,\sigma_1}(x)dx$$

Proposed restriction:

$$\int_{-\infty}^{0} g_{\mu_1,\sigma_1}(x)dx \leq 0.005$$

Theorem: 99% of the population described by $g_{\mu_i,\sigma_i}(x)$ will fall within the range: $(\mu_i-2.67\sigma_i) \leq x \leq (\mu_i+2.56\sigma_i)$ Thus: The maximum allowable value for $\sigma_i=(\mu_i/2.67)$ Therefore: $0<\sigma_i \leq (\mu_i/2.67)$, and $\mu_i>0$ 2.1.1 Cobalt Metal Surface Area as Predicted by the Bi-Modal Gaussian Crystallite Size Distribution According to the stated convention, the population of crystallites of size x nm=$[(\beta g_{\mu_1,\sigma 1}(x)+(-\beta)g_{\mu_2,\sigma_2}(x))]$ However, the surface area of a single crystallite of diameter x nm, is:

$[(\pi x^2)/2] (nm)^2$

Thus, the total surface area associated with crystallites of diameter x nm, is:

$[(1.571 x^2)(\beta g_{\mu_1,\sigma 1}(x)+(1-\beta)g_{\mu_2,\sigma_2}(x))](nm)^2$ Therefore, the total metal surface area of the complete population of metallic cobalt crystallites is:

$$\int_{0}^{\infty}[(1.571 \times 10^{-18}x^2)(\beta g_{\mu_1,\sigma_1}(x)+(1-\beta)g_{\mu_2,\sigma_2}(x))]dx \; m^2 \quad (4)$$

In addition, the volume of a single crystallite of diameter x nm, is $(0.083 \pi x^3)(nm)^3$.

Thus, the volume associated with crystallites of diameter x nm, is:

$[(0.2608 x^3)(\beta g_{\mu_1,\sigma 1}(x)+(1-\beta)g_{\mu_2,\sigma_2}(x))](nm)^3$ However, the density of metallic cobalt=8.9 g/ml. Therefore, the total mass of cobalt associated with crystallites of diameter x nm, is:

$[(2.32 \times 10^{-21} x^3)(\beta g_{\mu_1,\sigma 1}(x)+(1-\beta)g_{\mu_2,\sigma_2}(x))]g \quad (5)$ Thus, the total mass of cobalt contained in the complete population of metallic cobalt crystallites, is:

$$\int_{0}^{\infty}[(2.32 \times 10^{-21}x^3)(\beta g_{\mu_1,\sigma_1}(x)+(1-\beta)g_{\mu_2,\sigma_2}(x))]dx \; g \quad (6)$$

Equations 4 and 6 imply that the cobalt metal surface area per gram of metallic cobalt is:

$$677\left[\left(\int_{0}^{\infty}x^2(\beta g_{\mu_1,\sigma_1}(x)+(1-\beta)g_{\mu_2,\sigma_2}(x))dx\right)\bigg/ \left(\int_{0}^{\infty}x^3(\beta g_{\mu_1,\sigma_1}(x)+(1-\beta)g_{\mu_2,\sigma_2}(x))dx\right)\right] m^2/g \quad (7)$$

The application of equation (7) to the freshly reduced version of catalyst B implies that the cobalt metal surface area per gram of catalyst will be equal to:

$$98.8 \left[ \left( \int_0^\infty x^2 (\beta g_{\mu_1, \sigma_1}(x) + (1-\beta) g_{\mu_2, \sigma_2}(x)) dx \right) \middle/ \right. \quad (8)$$

$$\left. \left( \int_0^\infty x^3 (\beta g_{\mu_1, \sigma_1}(x) + (1-\beta) g_{\mu_2, \sigma_2}(x)) dx \right) \right] \text{ m}^2/\text{g}_{cat}$$

Equation (8) incorporates the following knowledge: 1 gram catalyst contains 0.195 gram cobalt, of which 75% reduces during the standard reduction procedure. Therefore, 1 gram catalyst B contains a total mass of 0.146 g metallic cobalt.

1.3.2.2 Fraction of the Total Amount of Metallic Cobalt Contained in Crystallites Larger than d nm (say $X_d$) Equation (6) Implies:

$$x_d = \left[ \left( \int_0^\infty x^3 (\beta g_{\mu_1, \sigma_1}(x) + (1-\beta) g_{\mu_2, \sigma_2}(x)) dx \right) \middle/ \right. \quad (9)$$

$$\left. \left( \int_0^\infty x^3 (\beta g_{\mu_1, \sigma_1}(x) + (1-\beta) g_{\mu_2, \sigma_2}(x)) dx \right) \right]$$

1.3.2.3 Estimation of Model Parameter Values Applicable to Freshly Reduced Catalyst B The proposed bi-modal Gaussian CSD model contains five parameters, ie $\mu_1$, $\sigma_1$, $\mu_2$, $\sigma_2$ and $\beta$. The two model parameters: $\mu_1$ and $\sigma_1$, determine the position and broadness of the first peak respectively. The two model parameters: $\mu_2$ and $\sigma_2$, fulfil the same function in the case of the second peak, whilst $\beta$ establishes the relative peak sizes.

During the application of this model to freshly reduced catalyst B, $\mu_1$ was fixed at 6 in answer to the requirement that 6 nm is the crystallite size of maximum abundance, as hereinbefore described. The remaining model parameters, $\sigma_1$, $\mu_2$, $\sigma_2$ and $\beta$, were selected on the basis of the following model fit criteria:

i) $\left[ \dfrac{98.8 \left( \int_0^\infty x^2 (\beta g_{\mu_1, \sigma_1}(x) + (1-\beta) g_{\mu_2, \sigma_2}(x)) dx \right)}{\left( \int_0^\infty x^3 (\beta g_{\mu_1, \sigma_1}(x) + (1-\beta) g_{\mu_2, \sigma_2}(x)) dx \right)} \right] \approx 11{,}9$ (refer: equation 8)

ii) $\left[ \dfrac{98.8 \left( \int_{15}^\infty x^3 (\beta g_{\mu_1, \sigma_1}(x) + (1-\beta) g_{\mu_2, \sigma_2}(x)) dx \right)}{\left( \int_0^\infty x^3 (\beta g_{\mu_1, \sigma_1}(x) + (1-\beta) g_{\mu_2, \sigma_2}(x)) dx \right)} \right] \approx 0{.}30$ (refer: equation 9)

A bi-modal metallic cobalt crystallite size distribution is thus proposed for the freshly reduced version of catalyst B. The bi-modal Gaussian crystallite size distribution model provides a reasonable description of this crystallite size distribution as gauged against the known characteristics as set out hereinbefore. The following model parameters were selected:

$\mu_1 = 6.0$
$\sigma_1 = 1.0$
$\mu_2 = 16.0$
$\sigma_2 = 5.0$
$\beta = 0.976$

The success of this set of model parameter values is illustrated in the Table 2:

TABLE 2

|  | Target value | Model prediction |
|---|---|---|
| Crystallite size of maximum abundance | 6 nm | 6 nm |
| Cobalt metal surface area | 11.9 m²/g cat | 11.9 m²/g cat |
| Mass % metallic cobalt contained in crystallites larger than 15 nm | 30% | 30.9% |

Figure 4:
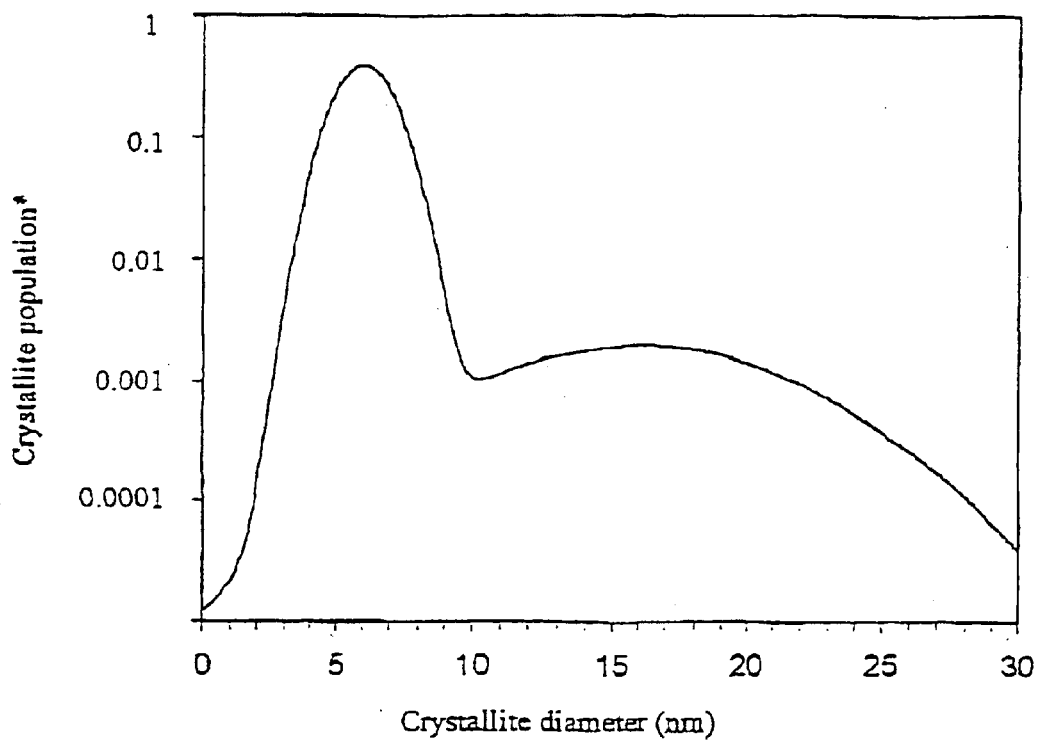
FIG. 4 is a proposed bi-modal Gaussian crystallite population present in a freshly reduced sample of catalyst B.

A visual illustration of the model derived crystallite distributions are provided by FIGS. 4 and 5.

1.4 Reconciliation of the Intrinsic Fischer-Tropsch Activity Profile (ie 2.1) and the Cobalt Crystallite Size Distribution (ie 1.3) of Catalyst B The relationship between the oxidation behaviour (ie both pre and ex $t_i$ oxidation) of the catalyst B during slurry phase synthesis at realistic conditions, and the time zero metallic cobalt crystallite size distribution was explored. The objective was to discover a metallic cobalt crystallite size distribution that should ensure complete resistance against oxidation during realistic slurry phase Fischer-Tropsch synthesis.

In 1.2, it was concluded that 9.8 m² cobalt metal surface area was lost per gram of catalyst due to pre $t_i$ oxidation (ie during phase 1 deactivation), and that (0.15 $a_t$) R.I.A.F. units were lost due to ex $t_i$ oxidation at 230° C. (ie during phases II and III deactivation).

However, a single R.I.A.F. unit corresponds to $1.72 \times 10^{-5}$ mole cobalt surface atoms per gram catalyst, a single metallic cobalt atom occupies 0.0662 nm² (assumed), and $a_t$=2.8 (based on a large number of Fischer-Tropsch slurry phase runs performed on catalyst B).

Accordingly, of the time zero cobalt metal surface area of 11.9 m² per gram of catalyst, 9.8 m² oxidized during catalyst induction (ie phase I deactivation) and was followed by the oxidation of an additional 0.29 m² during phase II and III deactivation as a consequence of slurry phase Fischer-Tropsch synthesis in a realistic environment.

Equation (8) was used to rationalize these values of 9.8 m²/g catalyst and 0.29 m²/g catalyst that were respectively lost during the deactivation mechanisms: pre $t_i$ oxidation and ex $t_i$ oxidation. The following assumptions were made: Metallic cobalt crystallites smaller than λ nm oxidize during catalyst induction (ie phase I deactivation); and metallic cobalt crystallites between λ and δ nm oxidize during catalyst conditioning (ie phases II and III deactivation). Thus, $$9{,}8 = \left[ \dfrac{98.8 \left( \int_0^\lambda x^2 (\beta g_{\mu_1, \sigma_1}(x) + (1-\beta) g_{\mu_2, \sigma_2}(x)) dx \right)}{\left( \int_0^\infty x^3 (\beta g_{\mu_1, \sigma_1}(x) + (1-\beta) g_{\mu_2, \sigma_2}(x)) dx \right)} \right] \quad (10)$$

$$0{,}29 = \left[ \dfrac{98.8 \left( \int_\lambda^\delta x^2 (\beta g_{\mu_1, \sigma_1}(x) + (1-\beta) g_{\mu_2, \sigma_2}(x)) dx \right)}{\left( \int_0^\infty x^3 (\beta g_{\mu_1, \sigma_1}(x) + (1-\beta) g_{\mu_2, \sigma_2}(x)) dx \right)} \right] \quad (11)$$

Bearing in mind that $\mu_1$=6.0; $\sigma_1$=1.0; $\mu_2$=16.0; $\sigma_2$=5.0 and $\beta$=0.976, both λ and δ were estimated from equations 10 and 11 as follows:

λ=8.24 nm
δ=10.30 nm

FIG. 6 provides a visual illustration of this result, indicating that the stability of the catalyst B, during realistic synthesis conditions, is provided by the metallic cobalt crystallites of size: >10.30 nm. It was thus surprisingly discovered that metallic cobalt crystallites up to 10.30 nm in size will oxidize during realistic Fischer-Tropsch synthesis conditions. This is in contradiction to published literature which recommends that a cobalt dispersion of 15% (ie a crystallite size range of 5–6 nm) is regarded as the optimum for the application of supported cobalt catalysts at typical Fischer-Tropsch synthesis conditions.

1.5 Optimum Metallic Cobalt Crystallite Size Distribution of a Supported Cobalt Catalyst with a 19.5 Mass % Cobalt Loading and a 75% Degree of Reduction (ie Comparable to Catalyst B)

The following three criteria were applied in order to quantify the concept of optimum:

A mono-modal Gaussian metallic cobalt crystallite size distribution as measured on the freshly reduced catalyst Maximum stabilized intrinsic Fischer-Tropsch activity during realistic synthesis conditions. A stabilized cobalt based Fischer-Tropsch catalyst is defined as a catalyst that has been conditioned completely during slurry phase Fischer-Tropsch synthesis at realistic conditions with an ultra pure synthesis gas. Furthermore, it is assumed that rejuvenatable poisoning is feed gas related as discussed so that oxidation is the exclusive deactivation mechanism during catalyst stabilization.

A Fischer-Tropsch synthesis effectiveness factor of ca 1

The mathematical equation describing a mono-modal Gaussian 'CSD' is:

$$f_{\mu,\sigma}(x) = (1/(\sigma\sqrt{2\pi}))e^{[-(x-\mu)^2/(2\sigma^2)]}, \text{ for all } x \quad (12)$$

where:

(a) $f_{\mu,\sigma}(x)$ = the crystallite population with a crystallite size of x nm.

(b) Imposed restriction:

$$\int_{-\infty}^{0} f_{\mu,\sigma}(x)dx > 0$$

is undesired from a physical point of view (ie crystallites with a negative diameter).

In order to accommodate this situation, a restriction was placed on the maximum attainable (ie neglible) value of:

$$\int_{-\infty}^{0} f_{\mu,\sigma}(x)dx$$

Proposed restriction:

$$\int_{-\infty}^{0} f_{\mu,\sigma}(x)dx \leq 0.005 \quad (13)$$

Thus, the crystallites of diameters $\geq 0$ always comprises $\geq 99.5\%$ of the total population. Further, 99% of the crystallite population will fall within the diameter range of:

$(\mu-2.67\sigma) \leq x \leq (\mu+2.67\sigma)$. Accordingly, the maximum allowable value for $\sigma=(\mu/2.67)$, and therefore $0<\sigma\leq(\mu/2.67)$, and $\mu \geq 0$ \quad (14)

The characteristics of the function: $f_{\mu,\sigma}(x)$, are thus:

i)

$$\frac{df(x)}{dx} = 0 \text{ at } x = \mu,$$

ie is the value of x at the function maximum ii)

$$\int_{-\infty}^{+\infty} f_{\mu,\sigma}(x)dx = 1, \text{ but: } \int_{-\infty}^{0} f_{\mu,\sigma}(x)dx \approx 0$$

iii) $f_{\mu,\sigma}(\mu-x) = f_{\mu,\sigma}(\mu+x)$

In the case of the freshly reduced catalyst:

The cobalt metal surface area of all crystallites larger than $\theta$ nm, is:

$$677\left[\left(\int_{\theta}^{\infty} x^2 e^{[-(x-\mu)^2/(2\sigma^2)]}dx\right) / \left(\int_{0}^{\infty} x^3 e^{[-(x-\mu)^2/(2\sigma^2)]}dx\right)\right] \quad (15)$$

$m^2$ per gram total metallic cobalt

In other words: The cobalt metal surface area of all crystallites larger than $\theta$ nm is:

$$98.8\left[\left(\int_{\theta}^{\infty} x^2 e^{[-(x-\mu)^2/(2\sigma^2)]}dx\right) / \left(\int_{0}^{\infty} x^3 e^{[-(x-\mu)^2/(2\sigma^2)]}dx\right)\right] m^2/g_{cat} \quad (16)$$

Equation (16) incorporates the following information:

1 gram catalyst contains 0.195 g cobalt, of which 75% is reduced. Thus, 1 gram catalyst corresponds to 0.146 g metallic cobalt.

Table 3 was constructed from equation 16, and applies to the freshly reduced state of the catalyst.

TABLE 3

| Selected mono-modal Gaussian CSD parameters of the freshly reduced catalyst | | Total cobalt metal surface areas ensphered by crystallites larger than θ nm, expressed in terms of m²/g catalyst | | |
|---|---|---|---|---|
| μ | σ | θ = 0 | θ = 8.24 | θ = 10.30 |
| 5 | 0.47 | 19.42 | 1.44 × 10⁻¹⁰ | 0 |
| 5 | 0.94 | 18.50 | 1.46 × 10⁻² | 6.71 × 10⁻¹⁰ |
| 5 | 1.40 | 17.25 | 0.50 | 5.55 × 10⁻⁷ |
| 5 | 1.87 | 15.86 | 1.89 | 0.17 |
| 7 | 0.66 | 13.87 | 0.61 | 8.74 × 10⁰ |
| 7 | 1.31 | 13.22 | 3.60 | 0.18 |
| 7 | 1.97 | 12.31 | 5.54 | 1.36 |
| 7 | 2.62 | 11.33 | 6.49 | 2.84 |
| 9 | 0.84 | 10.79 | 9.33 | 0.91 |
| 9 | 1.68 | 10.29 | 8.22 | 3.43 |
| 9 | 2.52 | 9.58 | 7.75 | 4.77 |
| 9 | 3.36 | 8.82 | 7.35 | 5.36 |
| 11 | 1.03 | 8.83 | 8.81 | 7.14 |
| 11 | 2.06 | 8.41 | 8.09 | 6.43 |
| 11 | 3.09 | 7.84 | 7.33 | 6.16 |
| 11 | 4.12 | 7.21 | 6.72 | 5.89 |
| 12 | 1.12 | 8.09 | 8.09 | 7.75 |
| 12 | 2.24 | 7.71 | 7.58 | 6.76 |
| 12 | 3.36 | 7.19 | 6.91 | 6.20 |
| 12 | 4.49 | 6.61 | 6.31 | 5.78 |
| 14 | 1.31 | 6.94 | 6.94 | 6.93 |
| 14 | 2.62 | 6.61 | 6.59 | 6.39 |

TABLE 3-continued

| Selected mono-modal Gaussian CSD parameters of the freshly reduced catalyst | | Total cobalt metal surface areas ensphered by crystallites larger than θ nm, expressed in terms of m²/g catalyst | | |
|---|---|---|---|---|
| μ | σ | θ = 0 | θ = 8.24 | θ = 10.30 |
| 14 | 3.93 | 6.16 | 6.06 | 5.80 |
| 14 | 5.24 | 5.66 | 5.54 | 5.31 |
| 16 | 1.50 | 6.07 | 6.07 | 6.07 |
| 16 | 3.00 | 5.78 | 5.78 | 5.73 |
| 16 | 4.50 | 5.39 | 5.35 | 5.25 |
| 16 | 5.99 | 4.96 | 4.90 | 4.79 |

The abovementioned table can be converted to R.I.A.F. through the incorporation of the following information:

(a) A single R.I.A.F unit corresponds to $1.72 \times 10^{-5}$ mole surface metallic cobalt atoms per gram catalyst, as hereinbefore described
(b) A single surface metallic cobalt atom occupies an area of $0.0662$ nm²

Thus, a single R.I.A.F. unit corresponds to 0.686 m² metallic cobalt surface area per gram catalyst (17)

The application of (17) enabled the construction of Table 4:

TABLE 4

| Selected mono-modal Gaussian CSD parameters of the freshly reduced catalyst | | Relative Intrinsic (Fischer-Tropsch) Activity Factor ('R.I.A.F.') | | |
|---|---|---|---|---|
| μ | σ | Time Zero | Time initial | Stabilized catalyst |
| 5 | 0.47 | 28.3 | 0.0 | 0.0 |
| 5 | 0.94 | 27.0 | 0.0 | 0.0 |
| 5 | 1.40 | 25.1 | 0.7 | 0.0 |
| 5 | 1.87 | 23.1 | 2.8 | 0.2 |
| 7 | 0.66 | 20.2 | 0.9 | 0.0 |
| 7 | 1.31 | 19.3 | 5.2 | 0.3 |
| 7 | 1.97 | 17.9 | 8.1 | 2.0 |
| 7 | 2.62 | 16.5 | 9.5 | 4.1 |
| 9 | 0.84 | 15.7 | 13.6 | 1.3 |
| 9 | 1.68 | 15.0 | 12.0 | 5.0 |
| 9 | 2.52 | 14.0 | 11.3 | 7.0 |
| 9 | 3.36 | 12.9 | 10.7 | 7.8 |
| 11 | 1.03 | 12.9 | 12.8 | 10.4 |
| 11 | 2.06 | 12.3 | 11.8 | 9.4 |
| 11 | 3.09 | 11.4 | 10.7 | 9.0 |
| 11 | 4.12 | 10.5 | 9.8 | 8.6 |
| 12 | 1.12 | 11.8 | 11.8 | 11.3 |
| 12 | 2.24 | 11.2 | 11.0 | 9.9 |
| 12 | 3.36 | 10.5 | 10.1 | 9.0 |
| 12 | 4.49 | 9.6 | 9.2 | 8.4 |
| 14 | 1.31 | 10.1 | 10.1 | 10.1 |
| 14 | 2.62 | 9.6 | 9.6 | 9.3 |
| 14 | 3.93 | 9.0 | 8.8 | 8.5 |
| 14 | 5.24 | 8.3 | 8.1 | 7.7 |
| 16 | 1.50 | 8.8 | 8.8 | 8.8 |
| 16 | 3.00 | 8.4 | 8.4 | 8.4 |
| 16 | 4.50 | 7.9 | 7.8 | 7.7 |
| 16 | 5.99 | 7.2 | 7.1 | 7.0 |

Figure 7:
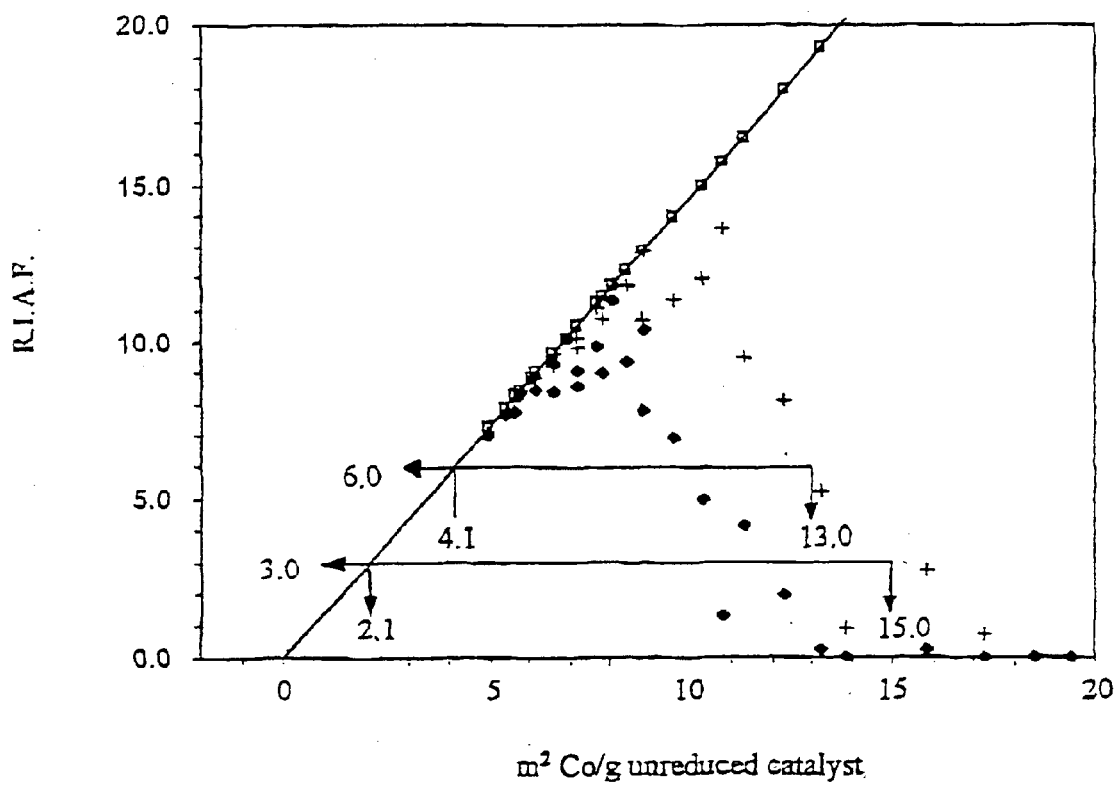
FIG. 7 is the relationship between the relative intrinsic (Fisher-Tropsch) activity factors and the specific metallic cobalt area of freshly reduced supported 19.5 mass % cobalt catalysts, displaying a mono-modal Gaussian crystallite size distribution.

A visual presentation of this section is presented as FIG. 7, and supports the following conclusions:

1. A 20 mass % supported cobalt Fischer-Tropsch catalyst will be optimum, if the freshly reduced catalyst answers the following criteria:
a) A degree of reduction of ca 75%
b) A mono-modal Gaussian metallic cobalt crystallite size distribution
c) A metallic cobalt surface area between 2.1 and 15.0 m², more preferred between 4.1 m² and 13.0 m² per gram of catalyst
d) A catalyst geometry (ie porosity, pore size distribution, etc) that will ensure a stabilized Fischer-Tropsch synthesis effectiveness factor of about 1
2. It should therefore be possible to prepare a 20 mass % supported cobalt Fischer-Tropsch catalyst with an initial R.I.A.F. (ie $a_i$) between 3.0 and 10.0, ie (2.4±1.3) times that of the catalyst B, which is characterized by an $a_i$ of 2.8.

1.6 Optimum Metallic Cobalt Crystallite Size Distributions of a Generic Supported Cobalt Catalyst with a Fischer-Tropsch Effectiveness Factor of 1 and a Reducible Cobalt Loading of Ω mass %, ie Reducible Under a Prescribed Catalyst Activation Procedure The same criteria as were applied in 1.5, were applied in order to quantify the concept of optimum.

The mathematical equations describing a mono-modal Gaussian CSD are presented in 1.5, ie equations: (12), (13), (14) and (15). In the case of the freshly reduced catalyst:

The cobalt metal surface of all crystallites larger than θ nm is:

$$(6.77 \, \Omega)\left[\left(\int_\theta^\infty x^2 e^{[-(x-\mu)^2/(2\sigma^2)]}dx\right) \bigg/ \left(\int_0^\infty x^3 e^{[-(x-\mu)^2/(2\sigma^2)]}dx\right)\right] \quad (18)$$

m²/g catalyst

Table 5 was constructed from equation (18) and applies to the freshly reduced state of the catalyst.

TABLE 5

| Selected mono-modal Gaussian CSD parameters of the freshly reduced catalyst | | Total cobalt metal surface areas ensphered by crystallites larger than θ nm, expressed in terms of m²/gram of catalyst | |
|---|---|---|---|
| μ | σ | θ = 0 | θ = 8.24 |
| 5 | 0.47 | 1.331 Ω | 0.000 Ω |
| 5 | 0.94 | 1.268 Ω | 0.001 Ω |
| 5 | 1.40 | 1.182 Ω | 0.034 Ω |
| 5 | 1.87 | 1.087 Ω | 0.130 Ω |
| 7 | 0.66 | 0.950 Ω | 0.042 Ω |
| 7 | 1.31 | 0.906 Ω | 0.247 Ω |
| 7 | 1.97 | 0.844 Ω | 0.380 Ω |
| 7 | 2.62 | 0.776 Ω | 0.445 Ω |
| 9 | 0.84 | 0.739 Ω | 0.639 Ω |
| 9 | 1.68 | 0.705 Ω | 0.563 Ω |
| 9 | 2.52 | 0.656 Ω | 0.531 Ω |
| 9 | 3.36 | 0.604 Ω | 0.504 Ω |
| 11 | 1.03 | 0.605 Ω | 0.604 Ω |
| 11 | 2.06 | 0.576 Ω | 0.554 Ω |
| 11 | 3.09 | 0.537 Ω | 0.502 Ω |
| 11 | 4.12 | 0.494 Ω | 0.460 Ω |
| 12 | 1.12 | 0.554 Ω | 0.554 Ω |
| 12 | 2.24 | 0.528 Ω | 0.519 Ω |
| 12 | 3.36 | 0.493 Ω | 0.473 Ω |
| 12 | 4.49 | 0.453 Ω | 0.432 Ω |
| 14 | 1.31 | 0.476 Ω | 0.476 Ω |
| 14 | 2.62 | 0.453 Ω | 0.452 Ω |
| 14 | 3.93 | 0.422 Ω | 0.415 Ω |
| 14 | 5.24 | 0.388 Ω | 0.380 Ω |
| 16 | 1.50 | 0.416 Ω | 0.416 Ω |
| 16 | 3.00 | 0.396 Ω | 0.396 Ω |

TABLE 5-continued

| Selected mono-modal Gaussian CSD parameters of the freshly reduced catalyst | | Total cobalt metal surface areas ensphered by crystallites larger than θ nm, expressed in terms of m²/gram of catalyst | |
|---|---|---|---|
| μ | σ | θ = 0 | θ = 8.24 |
| 16 | 4.50 | 0.369 Ω | 0.367 Ω |
| 16 | 5.99 | 0.340 Ω | 0.336 Ω |

The above mentioned table can be converted to R.I.A.F. through the incorporation of the following information:

(a) A single R.I.A.F. unit corresponds to $1.72 \times 10^{-5}$ mole surface metallic atoms per gram catalyst, as hereinbefore described (b) A single surface metallic cobalt atom occupies an area of $0.0662$ nm²

Thus, as also hereinbefore set out, a single R.I.A.F. unit corresponds to 0.686 m² metallic cobalt surface area per gram catalyst (19)

The application of (19) enabled the construction of Table 6:

TABLE 6

| Selected mono-modal Gaussian CSD parameters of the freshly reduced catalyst | | Relative Intrinsic (Fischer-Tropsch) Activity Factor (ie R.I.A.F.) | |
|---|---|---|---|
| μ | σ | Time zero | Time initial |
| 5 | 0.47 | 1.94 Ω | 0.00 Ω |
| 5 | 0.94 | 1.85 Ω | 0.00 Ω |
| 5 | 1.40 | 1.72 Ω | 0.05 Ω |
| 5 | 1.87 | 1.58 Ω | 0.19 Ω |
| 7 | 0.66 | 1.39 Ω | 0.06 Ω |
| 7 | 1.31 | 1.32 Ω | 0.36 Ω |
| 7 | 1.97 | 1.23 Ω | 0.55 Ω |
| 7 | 2.62 | 1.13 Ω | 0.65 Ω |
| 9 | 0.84 | 1.08 Ω | 0.93 Ω |
| 9 | 1.68 | 1.03 Ω | 0.82 Ω |
| 9 | 2.52 | 0.96 Ω | 0.77 Ω |
| 9 | 3.36 | 0.88 Ω | 0.73 Ω |
| 11 | 1.03 | 0.88 Ω | 0.88 Ω |
| 11 | 2.06 | 0.84 Ω | 0.81 Ω |
| 11 | 3.09 | 0.78 Ω | 0.73 Ω |
| 11 | 4.12 | 0.72 Ω | 0.67 Ω |
| 12 | 1.12 | 0.81 Ω | 0.81 Ω |
| 12 | 2.24 | 0.77 Ω | 0.76 Ω |
| 12 | 3.36 | 0.72 Ω | 0.69 Ω |
| 12 | 4.49 | 0.66 Ω | 0.63 Ω |
| 14 | 1.31 | 0.69 Ω | 0.69 Ω |
| 14 | 2.62 | 0.66 Ω | 0.66 Ω |
| 14 | 3.93 | 0.62 Ω | 0.61 Ω |
| 14 | 5.24 | 0.57 Ω | 0.55 Ω |
| 16 | 1.50 | 0.61 Ω | 0.61 Ω |
| 16 | 3.00 | 0.58 Ω | 0.58 Ω |
| 16 | 4.50 | 0.54 Ω | 0.53 Ω |
| 16 | 5.99 | 0.50 Ω | 0.49 Ω |

Figure 8:
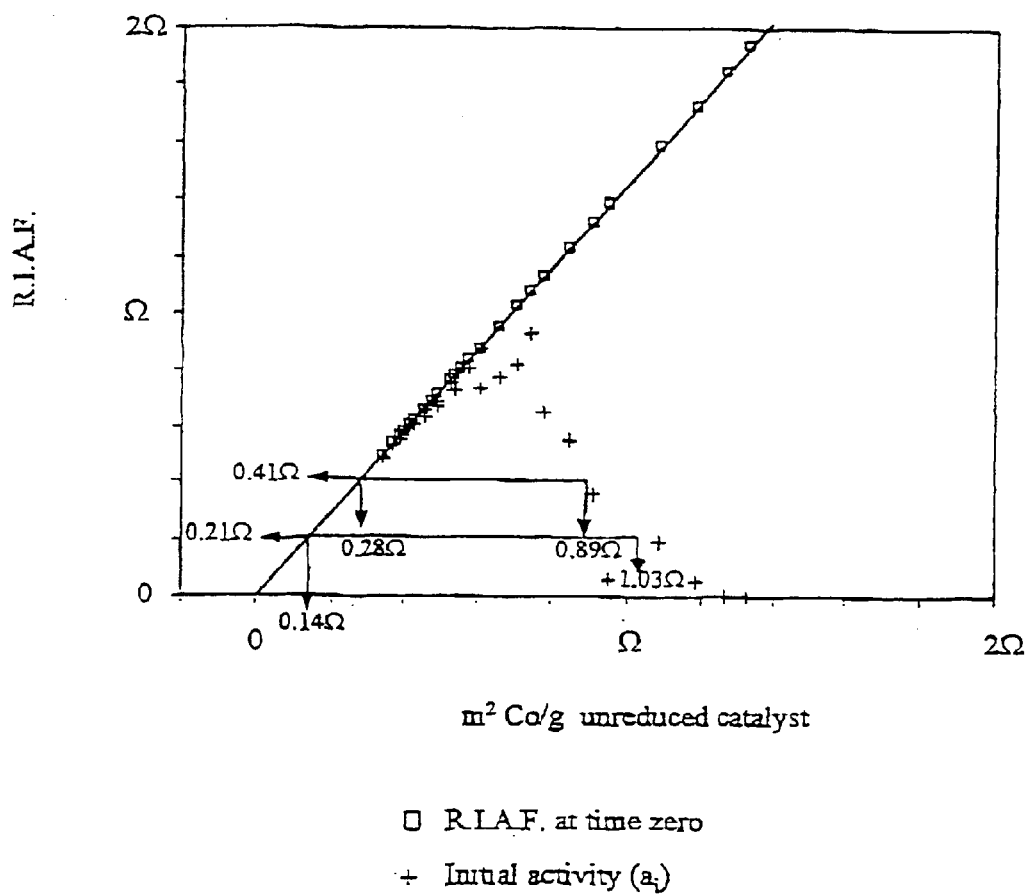
FIG. 8 is the relationship between the relative intrinsic (Fisher-Tropsch) activity factors and the specific metallic cobalt surface area of freshly reduced supported cobalt catalysts displaying a mono-modal Gaussian crystallite size distribution.

A visual presentation of this table is presented as FIG. 8, and supports the following conclusions:

1. A supported cobalt Fischer-Tropsch catalyst containing Ω mass % reducible. cobalt will be optimum, if the freshly reduced catalyst answers the following criteria:
(a) A mono-modal Gaussian metallic cobalt crystallite size distribution
(b) A metallic cobalt surface area, in m² per gram of catalyst, of from 0.0.14 Ω to 1.03 Ω, preferably from 0.28 Ω to 0.89 Ω.
(c) A catalyst geometry (ie porosity, pore size distribution, etc) that ensures a stabilized Fischer-Tropsch synthesis effectiveness factor of 1.

EXAMPLE 2

Example of $Al_2O_3$ Supported Cobalt Slurry Phase Catalyst in Accordance with the Invention (Catalyst F) that Displayed Enhanced Initial Intrinsic Fischer-Tropsch Activities Example 1 has shown that the optimum metallic cobalt crystallite size appears to be between 10 and 14 nm, and preferably is between 10 and 12 nm, ie. optimum from a maximum stabilized R.I.A.F, point of view. With the exception of metallic cobalt crystallite size distributions that peak between 8.2 nm and 10.3 nm the observed value for $a_i$ (ie R.I.A.F. at time initial) provides an accurate barometer for the expected stabilized R.I.A.F.

The objective with the identification of supported cobalt slurry phase Fischer-Tropsch catalysts with enhanced initial intrinsic activities, was the transformation of the bi-modal metallic cobalt crystallite size distribution ('CSD') of the freshly reduced sample of catalyst B into a mono-modal Gaussian type distribution with:

A metallic crystallite size of maximum abundance equal to 12±2 nm

A narrow distribution

If catalyst B is used as a benchmark, the successful increase of the average cobalt oxide crystallite size of the calcined catalyst precursor of an improved (m)gCo/(0.0025 m)gPt/100 gAl₂O₃ catalyst, could qualitatively be obtained from an associated easier reducibility. This statement is based on the known generality that the production of a highly dispersed and a highly reduced cobalt catalyst is difficult through the application of conventional catalyst preparation methods (eg impregnation with nitrate salt precursors). Conclusive confirmation of the successful tailoring of metallic cobalt crystallite size distributions, as measured on the freshly reduced catalysts, can be obtained through a combination of the following analytical techniques:

$H_2$ chemisorption

High Resolution Transmission Electron Microscopy (HRTEM)

Magnetic method

X-ray photoelectron spectroscopy (XPS)

Susceptibility towards oxidation under model $H_2/H_2O$ environments where cobalt bulk phase oxidation is thermodynamically impossible, as analyzed through the method of gravimetry.

Catalyst F was prepared in pursuit of this objective, ie the tailoring of cobalt oxide crystallite size distributions of calcined (m)gCo/(0.0025 m)gPt/100 gAl₂O₃ Fischer-Tropsch catalyst precursors.

Catalyst F (30 gCo/0.075 gPt/3.1 gBa/100 g Al₂O₃)

SASOL Germany GmbH's trademark product: Puralox SCCa 5/150 (i.e. a pre-shaped spherical porous Al₂O₃ catalyst support material) was modified during a barium nitrate impregnation step as follows:

2.86 g Ba(NO₃)₂ was dissolved in 50 ml distilled water. This solution was added to a 500 ml round ball flask in a rotavapor at 60° C., and 50 g of Puralox SCCa 5/150 was added. Aqueous slurry phase impregnation and vacuum drying was effected via the following procedure:

| Temperature of oil bath (° C.) | Rotavapor pressure (mbar) | Time (minutes) |
| --- | --- | --- |
| 60 | Atmospheric | 10 |
| 60 | 200 | 30 |
| 70 | 200 | 90 |
| 85 | 200 | 60 |
| 85 | 50 | 240 |

This vacuum dried Ba-modified intermediate product was subjected to a nation step, according to the following procedure:
Continuous air flow of 2.4 dm³$_n$/min
Temperature program:

The result of this exercise was a 3.1 gBa/100 Al$_2$O$_3$ modified support.

A 30 gCo/0.078 gPt/100 gAl$_2$O$_3$ slurry phase Fischer-Tropsch catalyst was prepared on the modified 3.1 gBa/100 gAl$_2$O$_3$ pre-shaped support material in accordance with the method of a aqueous slurry phase impregnation and vacuum drying, followed by direct fluidized bed calcination as disclosed in U.S. Pat. No. 5,733,839, WO 99/42214 and WO 00/20116.

In particular, the catalyst was prepared as follows:
29.3 g Co(NO$_3$)$_2$.6H$_2$O was dissolved in 28 ml distilled water and 0.0167 g (NH$_3$)$_4$Pt(NO$_3$)$_2$ was dissolved in 7 ml distilled water. These two solutions were mixed together in a 500 ml round ball flask in a rotavapor at 60° C. and atmospheric pressure, and 35.0 g of the 3.1 gBa/100 gAl$_2$O$_3$ modified pre-shaped support support was added. Aqueous slurry phase impregnation and vacuum drying was effected via the following procedure:

| Temperature of oil bath (° C.) | Rotavapor pressure (mbar) | Time (minutes) |
| --- | --- | --- |
| 60 | Atmospheric | 10 |
| 60 | 240 | 30 |
| 70 | 250 | 90 |
| 85 | 250 | 60 |
| 85 | 50 | 240 |

This vacuum dried intermediate was directly subjected to a fluidized bed calcination step, according to the following procedure:
Continuous air flow of 1.7 dm³$_n$/min
Temperature program:

35.1 g of this intermediate calcined material was subjected to the following 2$^{nd}$ cobalt/platinum impregnation and calcination step:
16.5 g Co(NO$_3$)$_2$.6H$_2$O was dissolved in 28 ml distilled water and 0.0273 g (NH$_3$)$_4$Pt(NO$_3$)$_2$ was dissolved in 7 ml distilled water. These two solutions were mixed together in a 500 ml round ball flask in a rotavapor at 60° C. and atmospheric pressure, and 35 g of the ex 1$^{st}$ cobalt/platinum impregnated and calcined intermediate was added. Aqueous slurry phase impregnation and vacuum drying was effected via the following procedure:

| Temperature of oil bath (° C.) | Rotavapor pressure (mbar) | Time (minutes) |
| --- | --- | --- |
| 60 | Atmospheric | 10 |
| 60 | 300 | 30 |
| 70 | 315 | 90 |
| 85 | 250 | 60 |
| 85 | 50 | 120 |

This vacuum dried intermediate product was directly subjected to a fluidized bed calcination step, according to the following procedure:
Continuous air flow of 1.7 dm³$_n$/min
Temperature program:

In preparation for laboratory scale slurry phase CSTR Fischer-Tropsch synthesis runs, this calcined catalyst precursor was reduced and wax coated in accordance with the procedure described for the preparation of catalyst B.

The intention behind the Al$_2$O$_3$ support modification of catalyst F was the manipulation of support acidity, based on the following:

Three of the five different types of surface hydroxyl groups, present on alumina, can serve as anchoring points for cobalt, ie acting as growth sites during the cobalt impregnation step. By limiting the surface concentration of potential cobalt crystallite growth points, whilst maintaining similar cobalt loadings per m² of the fresh support material larger cobalt crystallites should be obtained. Barium was identified as a promoter that could effectively reduce the surface hydroxyl concentration of Al$_2$O$_3$, as well as alternative support materials, such as: SiO$_2$, TiO$_2$, etc.

Support for this hypothesized beneficial promotion effect of barium was obtained through the magnetic method analysis performed on catalysts H and I. Catalysts H and I were prepared as follows:

Catalyst H (18 gCo/0.05 gPt/100 gAl$_2$O$_3$)

Puralox SCCa 5/150 (ie a pre-shaped Al$_2$O$_3$ supplied by SASOL Germany GmbH) was impregnated, vacuum dried and calcined with an aqueous Co(NO$_3$)$_2$ solution according to the method disclosed in U.S. Pat. No. 5,733,839, WO 99/42214 and WO 00/20116, incorporated herein by reference, on a laboratory scale. In particular, catalyst H was prepared as follows:

In a first impregnation step, a solution of 43.7 kg of cobalt nitrate (Co(NO$_3$)$_2$.6H$_2$O), 24.0 g of (NH$_3$)$_4$Pt(NO$_3$)$_2$ and 32.1 l of distilled water was mixed with 50.0 kg of Puralox SCCa 5/150 (ie a pre-shaped Al$_2$O$_3$ supplied by SASOL Chemie GmbH of Uberseering, Germany) by adding the support to the solution. The resultant slurry was added to a conical vacuum drier and continuously mixed. The temperature of this slurry was increased to 60° C. after which a vacuum of 20 kPa (a) was applied. During the first 3 hours of the drying step, the temperature was increased slowly and reached 95° C. after 3 hours. After 3 hours the vacuum was decreased to 3–15 kPa (a). The impregnated catalyst support was dried for 9 hours, after which this impregnated catalyst support was calcined at 250° C. for 6 hours. This catalyst preparation was limited to a single impregnation step, thus the relative low loading of 18 g Co/100 g $Al_2O_3$.

In preparation for its analysis via the Magnetic method, this calcined catalyst precursor was reduced and wax coated in accordance with the procedure described for the preparation of catalyst B.

Catalyst I (18.8 gCo/0.052 gPt/3.1 gBa/1.4 gSi/100 gAl$_2$O$_3$)

Puralox SCCa 5/150 (ie a pre-shaped $Al_2O_3$ catalyst support material supplied by SASOL Germany GmbH) was modified by means of a slurry phase tetra-ethoxy-silane (ie TEOS)/ethanol based impregnation and rotary kiln calcination step according to the method disclosed in WO 99/42214, incorporated herein by reference. In particular, the procedure was as follows:

32 g TEOS (tetra-ethoxy-silane) and 200 g EtOH was added to 200 g Puralox SCCa 5/150 (a pre-shaped $Al_2O_3$ catalyst support material supplied by SASOL Germany GmbH) by adding the support to the solution. In the impregnation step, the slurry was added to a vacuum drier and continuously mixed. The slurry was dried at a temperature of 100° C. with a pressure of 20 mbar being applied. Thereafter the dried impregnated support was calcined at 500° C. with a heating rate of 1° C./min and an airflow of 1.7 dm$^3_n$/min in a stainless steel calcination tube for 2 hours.

50 g of this modified support material was subsequently impregnated with 3 g Ba(NO$_3$)$_2$ and 30 ml H$_2$O by adding the support to the solution. In the impregnation step, the slurry was added to a vacuum drier and continuously mixed. The slurry was dried at a temperature of 100° C. with a pressure of 20 mbar being applied. Thereafter the dried impregnated modified support was calcined at 500° C. with a heating rate of 1° C./min and an airflow of 1.7 dm$^3_n$/min in a fluidized bed unit for 2 hours.

This 3.1 gBa/1.4 gSi/100 gAl$_2$O$_3$ pre-shaped support material was then impregnated, vacuum dried and calcined with an aqueous Co(NO$_3$)$_2$ solution according to the catalyst preparation procedure disclosed in U.S. Pat. No. 5,733,839, WO 99/42214 and WO 00/20116, incorporated herein by reference. In particular, Catalyst I was prepared as follows:

50 g of this modified pre-shaped support material was then mixed with 22.25 g Co(NO$_3$)$_2$.6H$_2$O and 25 mg Pt(NH$_3$)$_4$(NO$_3$)$_2$ and 50 ml H$_2$O by adding the support to the solution. In the impregnation step, the slurry was added to a vacuum drier and continuously mixed. The temperature of this slurry was increased to 100° C. and a vacuum of 20 mbar was applied for 2 hours. The dried impregnated material was calcined at 150° C. with a heating rate of 1° C./min for 1 hour and then increased to 250° C. with a heating rate of 1° C./min for 4 hours and an air flow of 1.7 dm$^3_n$/min.

This catalyst preparation was limited to a single impregnation step, thus the relative low loading of 18.8 gCo/100 gAl$_2$O$_3$.

In preparation for its analysis via the magnetic method, this calcined catalyst precursor was reduced and wax coated in accordance with the procedure described for the preparation of catalyst B.

The magnetic method analysis yielded the values as given in Table 7.

TABLE 7

| Catalyst | | Magnetic method results obtained on freshly reduced samples | |
|---|---|---|---|
| Number | Composition | Metallic cobalt crystallite size of maximum abundance | Mass % cobalt contained in metallic crystallites larger than 15 nm |
| H | 18 g Co/0.05 g Pt/ 100 g support | 6.1 ± 0.8 | 29 ± 3 |
| I | 18.5 g Co/0.05 g Pt/ 3.1 g Ba/100 g support | 8 | 21 |

Figure 9:
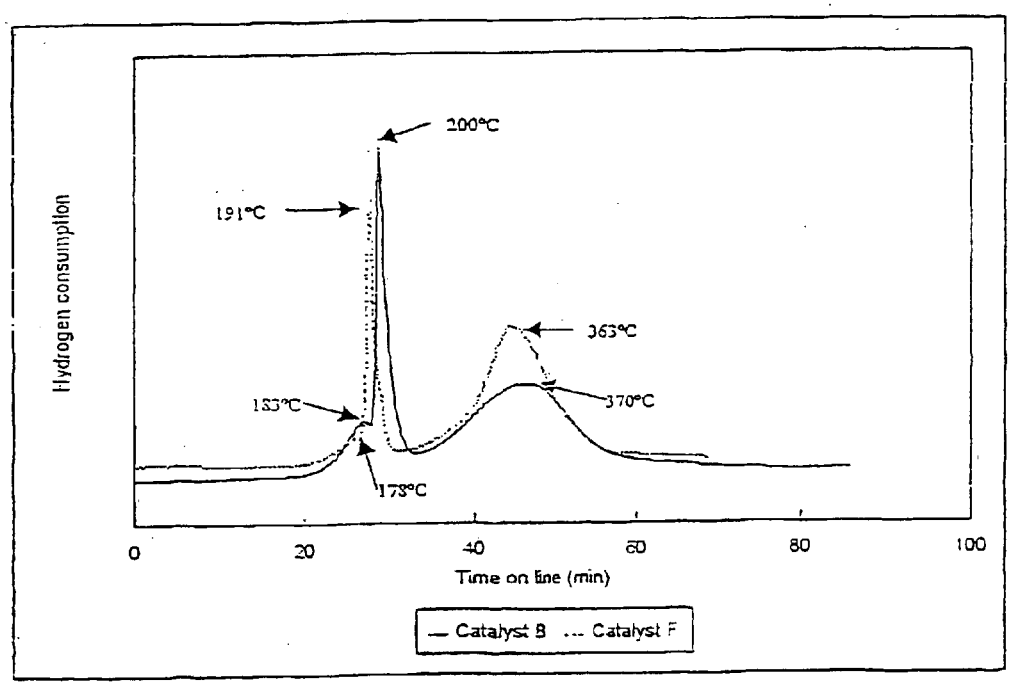
FIG. 9 is a superimposition of the temperature programmed reduction profiles of the finally calcined catalyst precursors of catalyst B and catalyst F.

The apparent discrepancy illustrated in FIG. 9 (ie the barium promoted catalyst precursor not being markedly more reducible), may be due to an artifact that was caused by some barium that could have dissolved into the cobalt impregnation solution. The barium impregnated and dried intermediate of catalyst F was specifically calcined at the relative high temperature of 600° C. in an attempt to strengthen the bond between alumina and barium. This objective was also enforced by published concerns that cobalt based Fischer-Tropsch catalytic activities are sensitive towards alkaline promotion, and that the structural promotion of cobalt catalysts by, for example magnesia, generally impedes reduction.

It can thus be concluded that Catalyst F all showed qualitative evidence of improved metallic cobalt crystallite size distributions, a characteristic that was expected to produce slurry phase Fischer-Tropsch catalysts of enhanced initial intrinsic activities, and thus also stabilized R.I.A.F.'s.

The expectation expressed in this conclusion was confirmed, as depicted in Table 8:

TABLE 8

Title: The slurry phase CSTR Fischer-Tropsch synthesis performance data of the cobalt catalyst: F

| Catalyst number | F |
|---|---|
| Catalyst characteristics: | |
| i) Composition | 30 g Co/0.075 g Pt/ 3.1 g Ba/100 g Al$_2$O$_3$ |
| ii) Mass % Co (ie as measured in the finally calcined precursor) | 17.4 |
| iii) Mass % reducible Co (ie expressed with respect to the state of the finally calcined precursor) | 13.1* |
| iv) Co metal surface area as determined through H$_2$ chemisorption (m$^2$/gram catalyst) | 9.7 |
| Synthesis performance data: | |
| Run analysis number | 48£ |
| Time on stream (hours) | 15 |
| % (H$_2$ + CO) conversion | 51 |
| Reactor partial pressures: | |
| H$_2$ (bar) | 6.5 |
| CO (bar) | 3.7 |
| H$_2$O (bar) | 3.2 |
| CO$_2$ (bar) | 0.2 |
| Initial Relative Intrinsic (Fischer-Tropsch) Activity Factor (ie: a$_i$ = R.I.A.F. at t$_i$) | 3.6 |

*Note:
A degree of reduction of 75% is assumed

The following conclusions were drawn from Table 8 in combination with FIG. 8:

Catalyst F

Catalyst F displayed an initial intrinsic Fischer-Tropsch activity of 3.6 R.I.A.F. units. This was achieved with a cobalt loading of 30 g per 100 $gAl_2O_3$.

The relative enhancement of $a_i$, as effected through the preparation method of catalyst F, is quantified in Table 9:

TABLE 9

| | $a_i$ (R.I.A.F at time initial) |
|---|---|
| Catalyst F | 3.6 |
| Catalyst B with a 10.0 mg $Co(NO_3)_2.6H_2O$ per $m^2$ (fresh) $Al_2O_3$ loading | 2.8 |

Catalyst F contained 13.1 mass % reducible cobalt, implying that FIG. 5 can be applied to catalyst F by replacing $\Omega$ with 13.1. The cobalt metal surface area of freshly reduced catalyst F was estimated as 9.7 $m^2/g$ catalyst, implying a maximum attainable $a_i$ of ca 10.0.

The above-mentioned conclusions are consolidated in Table 10:

TABLE 10

| | Initial intrinsic Fischer-Tropsh activities | |
|---|---|---|
| | Expressed as a multiple of that of catalyst B | Expressed as a percentage of that of the ideal* supported cobalt Fischer-Tropsch catalyst |
| Catalyst F | 1.29 | ca 36 |

*Note:
An ideal supported cobalt Fischer-Tropsch catalyst displays the following characteristics:
a) A mono-modal metallic cobalt crystallite size distribution in case of the freshly reduced sample
b) A catalyst with a Fischer-Tropsch synthesis effectiveness factor of 1 in the case of the stabilized catalyst.

EXAMPLE 3

Not in Accordance with the Invention

Catalyst K (30 gCo/0.075 gPt/3 gF/100 $gAl_2O_3$)

Sasol Germany GmbH's trademark product: Puralox SCCa 5/150 (i.e. a pre-shaped spherical porous $Al_2O_3$ catalyst support material) was modified during a hydrofluoride impregnation step as follows:

3 g of a 48% hydrofluoride acid solution was mixed with 50 ml. distilled water in a teflon beaker. This solution was added to 50 g of Puralox 5/150 in a 500 ml round ball flask in a rotorvapor at 60° C. Aqueous slurry phase impregnation and vacuum drying was effected via the following procedure:

| Temperature of oil bath (° C.) | Rotorvapor pressure (mbar) | Time (minutes) |
|---|---|---|
| 60 | Atmospheric | 10 |
| 60 | 200 | 30 |
| 70 | 200 | 90 |
| 85 | 200 | 60 |
| 85 | 50 | 240 |

This vacuum dried F-modified intermediate product was subjected to a fluidised bed calcination step, according to the following procedure:

Continuous air flow of 2.4 $dm^3_n$/min

Temperature program:
From 25° C. to 500° C. at 1.6° C./min and keeping it at 500° C. for 4 hours The result of this exercise was a 3 gF/100 $gAl_2O_3$ modified support.

A 30 gCo/0.075 gPt/100 $gAl_2O_3$ slurry phase Fischer-Tropsch catalyst was prepared on the modified 3 gF/100 $gAl_2O_3$ pre-shaped support material in accordance with the method of an aqueous slurry phase impregnation and drying, followed by direct fluidised bed calcination as disclosed in U.S. Pat. No. 5,733,839, WO 99/42214 and WO 00/20116.

In particular the catalyst was prepared as follows:

29.3 g $Co(NO_3)_2.6H_2O$ was dissolved in 28 ml distilled water and 0.0167 g $(NH_3)_4Pt(NO_3)_2$ was dissolved in 7 ml distilled water. These two solutions were mixed together in a 500 ml round ball flask in a rotorvapor at 60° C. and atmospheric pressure, and 35.0 g of the 3 gF/100 $gAl_2O_3$ modified pre-shaped support was added. Aqueous slurry phase impregnation and vacuum drying was effected via the following procedure:

| Temperature of oil bath (° C.) | Rotorvapor pressure (mbar) | Time (minutes) |
|---|---|---|
| 60 | Atmospheric | 10 |
| 60 | 200 | 30 |
| 70 | 200 | 90 |
| 85 | 200 | 60 |
| 85 | 50 | 240 |

This vacuum dried intermediate was directly subjected to a fluidized bed calcination step, according to the following procedure:

Continuous air flow of 1.7 $dm^3_n$/min

Temperature program:
From 25° C. to 250° C. at 1° C./min and keeping it at 250° C. for 6 hours 35.0 g of this intermediate calcined material was subjected to the following $2^{nd}$ cobalt/platinum impregnation and calcination step:

16.5 g $Co(NO_3)_2.6H_2O$ was dissolved in 28 ml distilled water and 0.0273 g $(NH_3)_4Pt(NO_3)_2$ was dissolved in 7 ml distilled water. These two solutions were mixed together in a 500 ml round ball flask in a rotarvapor at 60° C. and atmospheric pressure, and 35.0 g of the ex $1^{st}$ cobalt/platinum impregnated and calcined intermediate was added. Aqueous slurry phase impregnation and vacuum drying was effected via the following procedure:

| Temperature of oil bath (° C.) | Rotorvapor pressure (mbar) | Time (minutes) |
|---|---|---|
| 60 | Atmospheric | 10 |
| 60 | 200 | 30 |
| 70 | 200 | 90 |
| 85 | 200 | 60 |
| 85 | 50 | 240 |

This vacuum dried intermediate was directly subjected to a fluidized bed calcination step, according to the following procedure:

Continuous air flow of 1.7 $dm^3_n$/min

Temperature program:
From 25° C. to 250° C. at 1° C./min and keeping it at 250° C. for 6 hours In preparation for laboratory scale slurry phase CSTR Fischer-Tropsch synthesis runs, this calcined catalyst precursor was reduced and wax coated in accordance with the procedure described for catalyst B.

This catalyst was also tested for Fischer-Tropsch synthesis behaviour (table 13) and no influence of the fluoride promotion on the intrinsic Fischer-Tropsch performance of the catalyst was observed.

This observation can be explained by the fact that, in contradiction to barium, fluoride is not bonding to the hydroxyl groups that are used for anchoring of the cobalt crystallites, but fluoride is bonding to other hydroxyl groups. Fluoride is, therefore, not influencing the cobalt crystallite size distribution and thus the intrinsic Fischer-Tropsch activity.

TABLE 13

| Catalyst | K |
|---|---|
| Catalyst characteristics: | |
| i) Composition | 30 g Co/0.075 g Pt/ 3 g F/100 g Al$_2$O$_3$ |
| ii) Mass % Co (ie as measured in the finally calcined precursor) | 19.0 |
| iii) Mass % reducible Co (ie expressed with respect to the state of the finally calcined precursor) | 14.3* |
| Synthesis performance data: | |
| Run analysis number | 11£ |
| Time on stream (hours) | 15 |
| % (H$_2$ + CO) conversion | 64 |
| Reactor partial pressures: | |
| H$_2$ (bar) | 5.3 |
| CO (bar) | 3.0 |
| H$_2$O (bar) | 4.6 |
| CO$_2$(bar) | 0.2 |
| Initial Relative Intrinsic (Fischer-Tropsch) Activity Factor (ie: a$_i$ = R.I.A.F. at t$_i$) | 3.0 |

*Note:
A degree of reduction of 75% is assumed

EXAMPLE 4
Examples of Al$_2$O$_3$ Supported Cobalt Slurry Phase Catalyst Samples in Accordance with the Invention (Catalysts E and G) That Displayed Enhanced Initial Intrinsic Fischer-Tropsch Activities Catalyst samples E and G were prepared in pursuit of this objective mentioned above, ie the tailoring of cobalt oxide crystallite size distributions of calcined (m)gCo/(0.0025 m)gPt/100 gAl$_2$O$_3$ Fischer-Tropsch catalyst precursors.
Catalyst E (40 gCo/0.1 gPt/100 gAl$_2$O$_3$)

SASOL Germany GmbH's trademark product: Puralox SCCa 5/150 (ie a pre-shaped spherical porous Al$_2$O$_3$ catalyst support material), was coated with a uniform carbon based layer at KataLeuna GmbH Catalysts (Am Haupttor; D-06236 Leuna; Germany) in accordance with a method as described in EP 0681868, incorporated herein by reference. The result of this exercise was a 12.4 gC/100 gAl$_2$O$_3$ modified support.

A 40 gCo/0.100 gPt/100 gAl$_2$O$_3$ slurry phase Fisher-Tropsch catalyst was prepared on this modified 12.4 gC/100 gAl$_2$O$_3$ pre-shaped support material in accordance with the method of aqueous slurry phase impregnation and vacuum drying, followed by direct fluidized bed calcination disclosed in U.S. Pat. No. 5,733,839, WO 99/42214 and WO 00/20116, incorporated herein by reference. In particular, catalyst E was prepared as follows:

34.1 g Co(NO$_3$)$_2$.6H$_2$O was dissolved in 40 ml distilled water and 0.0185 g (NH$_3$)$_4$Pt(NO$_3$)$_2$ was dissolved in 10 ml distilled water. These two solutions were mixed together in a 500 ml round bail flask in a rotavapor at 60° C. and atmospheric pressure, and 50 g of the 12.4 g C/100 g Al$_2$O$_3$ modified support was added. Aqueous slurry phase impregnation and vacuum drying was effected via the following procedure:

| Temperature of oil bath (° C.) | Rotavapor pressure (mbar) | Time (minutes) |
|---|---|---|
| 60 | Atmospheric | 10 |
| 60 | 240 | 30 |
| 70 | 240 | 90 |
| 85 | 240 | 60 |
| 85 | 50 | 240 |

This vacuum dried intermediate product was directly subjected to a fluidized calcination step, having followed the following procedure:
Continuous air flow of 1.7 dm$^3_n$/min
Temperature program:

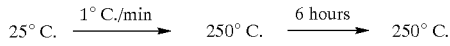

50 g of this intermediate calcined material was subjected to the following 2$^{nd}$ cobalt/platinum impregnation and calcination step:

34.1 g Co(NO$_3$)$_2$.6H$_2$O was dissolved in 40 ml distilled water and 0.0189 g (NH$_3$)$_4$Pt(NO$_3$)$_2$ was dissolved in 10 ml distilled water. These two solutions were mixed together in a 500 ml round ball flask in a rotavapor at 60° C. and atmospheric pressure, and 50 g of the ex 1$^{st}$ impregnated and calcined intermediate was added. Aqueous slurry phase impregnation and vacuum drying was effected in the same manner as during the 1$^{st}$ cobalt/platinum impregnation step. This vacuum dried intermediate product was directly subjected to a fluidized bed calcination step, having followed the following procedure:
Continuous air flow of 1.7 dm$^3_n$/min
Temperature program:

50 g of this intermediate calcined material was subjected to the following 3$^{rd}$ cobalt/platinum impregnation and calcination step: 25.4 g Co(NO$_3$)$_2$.6H$_2$O was dissolved in 40 ml distilled water and 0.0446 g (NH$_3$)$_4$Pt(NO$_3$)$_2$ was dissolved in 10 ml distilled water. These two solutions were mixed together in a 500 ml round ball flask in a rotavapor at 60° C. and atmospheric pressure, and 50 g of the ex 2$^{nd}$ impregnated and calcined intermediate was added. Aqueous slurry phase impregnation and vacuum drying was effected in the same manner as during the 1$^{st}$ cobalt/platinum impregnation step. This vacuum dried intermediate product was directly subjected to a fluidized bed calcination step, having followed the following procedure:
Continuous air flow of 1.7 dm$^3_n$/min
Temperature program:

A total of three consecutive impregnation steps were thus performed as dictated by the restrictions imposed by the pore volume of the solid materials.

In preparation for laboratory scale slurry phase CSTR Fischer-Tropsch synthesis runs, this calcined catalyst precursor was reduced externally at 350° C. For this purpose 22 μg of the catalyst was reduced at 1 bar pure $H_2$ (space velocity of 2000 $ml_n$/g catalyst.h), whilst the temperature was increased from 25° C. to 350° C. at a rate of 1° C./min, where-after the temperature was kept constant at 350° C. for 16 hours.

The reduced catalyst was allowed to cool down to room temperature where the hydrogen was replaced by argon and the catalyst was unloaded in molten wax under the protection of an argon blanket. This wax coated catalyst was then transferred to the slurry synthesis reactor.

Catalyst G (30 gCo/0.075 gPT/100 g$Al_2O_3$)

A Pt promoted cobalt catalyst was prepared on SASOL Germany GmbH's trademark product: Puralox SCCa 5/150 as the selected pre-shaped support material, in accordance with the method of aqueous slurry phase impregnation and vacuum drying, followed by direct fluidized bed calcination disclosed in U.S. Pat. No. 5,733,839, WO 99/42214 and WO 00/20116. In particular, the catalyst was prepared as follows:

44.6 g $Co(NO_3)_2 \cdot 6H_2O$ was dissolved in 40 ml distilled water and 0.0248 g $(NH_3)_4Pt(NO_3)_2$ was dissolved in 10 ml distilled water. These two solutions were mixed together in a 500 ml round ball flask in a rotavapor at 60° C. and atmospheric pressure, and 50 g of the Puralox SCCa 5/150 support material was added. Aqueous slurry phase impregnation and vacuum drying was effected via the following procedure:

| Temperature of oil bath (° C.) | Rotavapor pressure (mbar) | Time (minutes) |
|---|---|---|
| 60 | Atmospheric | 10 |
| 60 | 240 | 30 |
| 70 | 244 | 90 |
| 85 | 242 | 60 |
| 85 | 50 | 240 |

This vacuum dried intermediate product was directly subjected to a fluidized bed calcination step according to the following procedure:

Continuous air flow of 1.7 $dm^3_n$/min

Temperature program:

This calcined intermediate product of the $1^{st}$ cobalt/platinum impregnation and calcination step was then subjected to a partial reduction step prior to the $2^{nd}$ (and last) cobalt/platinum impregnation step. For this purpose this intermediate material was reduced at 1 bar pure hydrogen (space velocity of 2000 $ml_n$/g intermediate.h) whilst the temperature was increased from 25° C. to 230° C. at a rate of 1° C./min temperature was kept constant at 230° C. for 2 hours.

35.0 g of this partially reduced intermediate material was transferred to the aqueous impregnation solution of the $2^{nd}$ cobalt/platinum impregnation step under the protection of an argon blanket, an impregnation solution that was prepared as follows:

22.7 g $Co(NO_3)_2 \cdot 6H_2O$ was dissolved in 28 ml distilled water and 0.0401 g $(NH_3)_4Pt(NO_3)_2$ was dissolved in 7 ml distilled water. These two solutions were mixed together in a 500 ml round ball flask in a rotavapor at 60° C. and atmospheric pressure.

Aqueous slurry phase impregnation and vacuum drying was effected via the following procedure:

| Temperature of oil bath (° C.) | Rotavapor pressure (mbar) | Time (minutes) |
|---|---|---|
| 60 | Atmospheric | 10 |
| 60 | 300 | 30 |
| 70 | 307 | 90 |
| 85 | 301 | 60 |
| 85 | 50 | 240 |

This vacuum dried intermediate product was directly subjected to a fluidized calcination step, according to the following procedure:

Continuous air flow of 1.7 $dm^3_n$/min

Temperature program:

In preparation for laboratory scale slurry phase CSTR Fischer-Tropsch synthesis runs, the finally calcined catalyst precursor was reduced and wax coated in accordance with the procedure described for the preparation of catalyst B.

Figure 10:
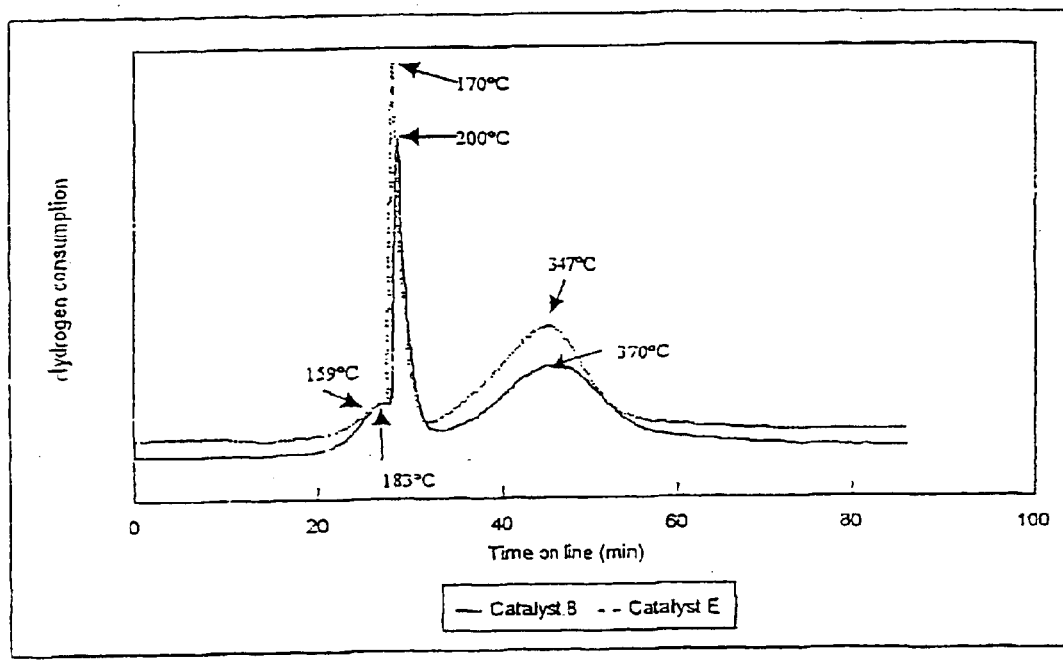
FIG. 10 is a superimposition of the temperature programmed reduction profiles of the finally calcined catalyst precursors of catalyst B and catalyst E.
Figure 11:
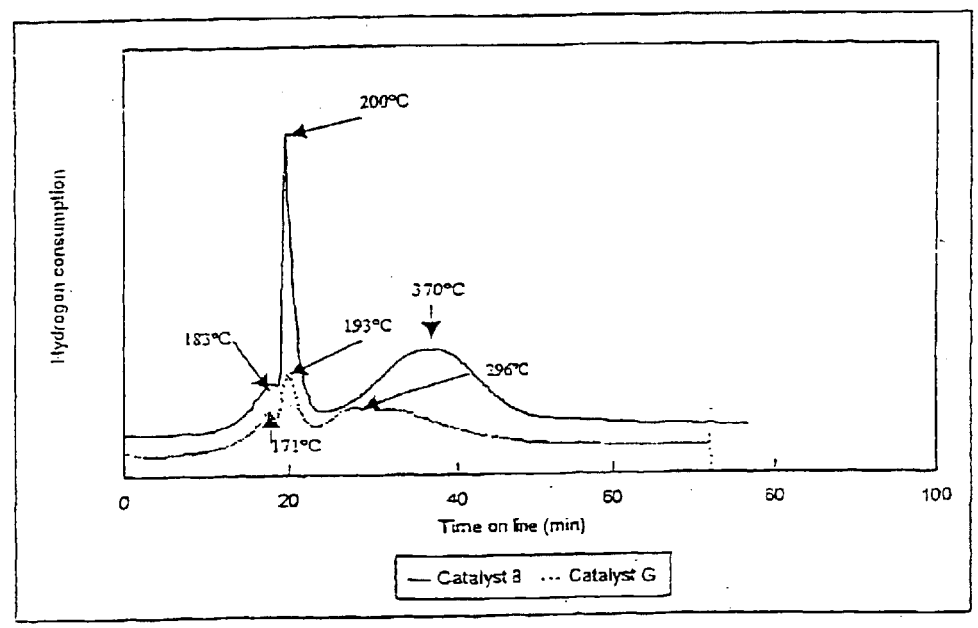
FIG. 11 is a superimposition of the temperature programmed reduction profiles of the finally calcined catalyst precursors of catalyst B and catalyst G.

The Temperature Programmed Reduction (ie TPR) profiles of catalysts E and g (FIGS. 10 and 11) are in line with the anticipation that an easier reducibility is a qualitative indication of an increase in the average cobalt oxide crystallite size, as also explained in example 2. An enhancement in the initial intrinsic Fischer-Tropsch activity, in line with FIG. 8 was anticipated.

It can thus be concluded that Catalysts E and G all showed qualitative evidence of improved metallic cobalt crystallite size distributions, a characteristic that was expected to produce slurry phase Fischer-Tropsch catalysts of enhanced initial intrinsic activities, and thus also stabilized R.I.A.F.'s.

The expectation expressed in this conclusion was confirmed, as depicted in Table 14:

TABLE 14

Title: The slurry phase CSTR Fischer-Tropsch synthesis performance data of the cobalt catalyst: E and G

| Catalyst number | E | G |
|---|---|---|
| Catalyst characteristics: | | |
| i) Composition | 40 g Co/0.100 g Pt/ 100 g $Al_2O_3$ | 30 g Co/0.075 g Pt/ 100 g $Al_2O_3$ |
| ii) Mass % Co (ie as measured in the finally calcined precursor) | 22.6 | 18.6 |
| iii) Mass % reducible Co (ie expressed with respect to the state of the finally calcined precursor) | 17.0* | 14.0* |
| (iv) Co metal surface area as determined through $H_2$ chemisorption ($m^2$/gram catalyst) | 14.9 | 12.9 |
| Synthesis performance data: | | |
| Run analysis number | 45£1 | 46£1 |
| Time on stream (hours) | 15 | 15 |
| % ($H_2$ + CO) conversion | 76 | 65 |

TABLE 14-continued

Title: The slurry phase CSTR Fischer-Tropsch synthesis performance data of the cobalt catalyst: E and G

| Catalyst number | E | G |
|---|---|---|
| Reactor partial pressures: | | |
| $H_2$ (bar) | 4.0 | 5.0 |
| CO (bar) | 2.3 | 2.9 |
| $H_2O$ (bar) | 5.9 | 4.4 |
| $CO_2$ (bar) | 0.5 | 0.3 |
| Initial Relative Intrinsic (Fischer-Tropsch) Activity Factor (ie: $a_i$ = R.I.A.F. at $t_i$) | 5.6 | 4.7 |

*Note:
A degree of reduction of 75% is assumed

Figure 12:
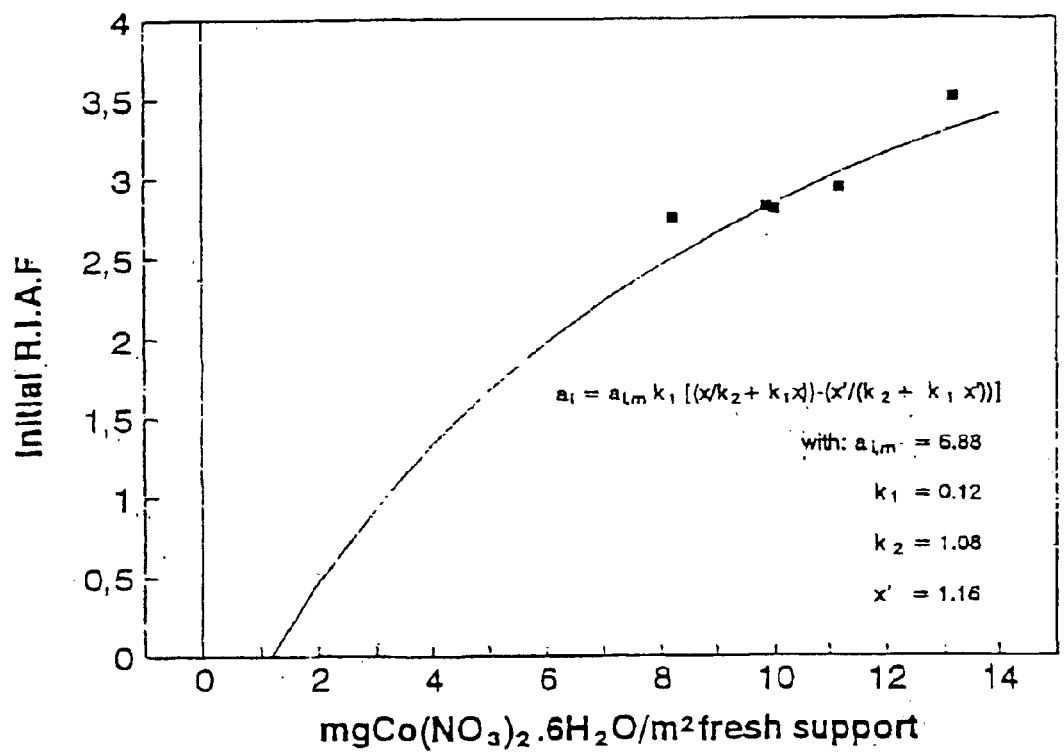
FIG. 12 is a correlation between observed initial relative intrinsic activity factors of $Co/Al_2O_3$ slurry phase Fischer-Tropsch catalyst E and the total $Co(NO_3)_2.6H_2O$ loading per $m^2$ of SASOL Germany GmbH's product: Puralox SCCa 5/150.

The following conclusions were drawn from Table 14 in combination with FIGS. 8 and 12:

Catalyst E:

Catalyst E displayed an initial intrinsic Fischer-Tropsch activity of 5.6 R.I.A.F. units. This was achieved with a cobalt loading of 40 g per 100 $gAl_2O_3$.

In the case of catalyst B, a cobalt loading of 30 gCo/100 $gAl_2O_3$ was postulated as the optimum for a catalyst prepared on SASOL Germany GmbH's products: Puralox SCCa 5/150, that is limited to a maximum of two aqueous phase $Co(NO_3)_2$ impregnation steps. This preferred pre-shaped spherical $Al_2O_3$ support material is characterized by a surface area of 150±10 $m^2/g$, implying that a 30 gCo/100 $gAl_2O_3$ catalyst corresponds to a $Co(NO_3)_2.6H_2O$ loading of 10 $mg/m^2$ fresh $Al_2O_3$. Catalyst B is, however, also characterized by an $a_i$ of 2.8±0.2. FIG. 12 was constructed from the combination of this knowledge with the $a_i$'s derived from other slurry Fischer-Tropsch synthesis run numbers.

The relative enhancement of $a_i$, as effected through the preparation method of catalyst E, is quantified in Table 15:

TABLE 15

| | $a_i$ (R.I.A.F at time initial) |
|---|---|
| Catalyst E | 5.6 |
| Catalyst B with a 13.3 mg $Co(NO_3)_2.6H_2O$ per $m^2$ (fresh) $Al_2O_3$ loading | 3.3* |

*Note:
estimated from the best fitted equation indicated on FIG. 12
Catalyst E contained 17.0 mass % reducible cobalt, implying that FIG. 8 can be applied to catalyst E by replacing Ω with 17.0. The cobalt metal surface area of freshly reduced catalyst E was estimated as 14.9 $m^2/g$ catalyst, implying a maximum attainable $a_i$ of ca 7.5.

Catalyst G

Catalyst G displayed an initial intrinsic Fischer-Tropsch activity of 4.7 R.I.A.F. units. This was achieved with a cobalt loading of 30 g per 100 $gAl_2O_3$.

The relative enhancement of $a_i$, as effected through the preparation method of catalyst G, is quantified in Table 16:

TABLE 16

| | $a_i$ (R.I.A.F at time initial) |
|---|---|
| Catalyst G | 4.7 |
| Catalyst B with a 10.0 mg $Co(NO_3)_2.6H_2O$ per $m^2$ (fresh) $Al_2O_3$ loading | 2.8* |

*Note:
estimated from the best fitted equation indicated on FIG. 12
Catalyst G contained 14.0 mass % reducible cobalt, implying that FIG. 8 can be applied to catalyst G by replacing Ω with 14.0. The cobalt metal surface area of freshly reduced catalyst G was estimated as 12.9 $m^2/g$ catalyst, implying a maximum attainable $a_i$ of ca 4.3.

The above-mentioned conclusions are consolidated in Table 17:

TABLE 17

| | Initial intrinsic Fischer-Tropsh activities | |
|---|---|---|
| | Expressed as a multiple of that of catalyst B | Expressed as a percentage of that of the ideal* supported cobalt Fischer-Tropsch catalyst |
| Catalyst E | 1.70 | ca 75 |
| Catalyst G | 1.68 | ca 100 |

*Note:
An ideal supported cobalt Fischer-Tropsch catalyst displays the following characteristics:
a) A mono-modal metallic cobalt crystallite size distribution in the case of the freshly reduced sample
b) A catalyst with a Fischer-Tropsch synthesis effectiveness factor of 1 in the case of the stabilized catalyst.

What is claimed is:

1. A cobalt based Fischer-Tropsch catalyst, the catalyst including a porous catalyst support and metallic cobalt crystallites within the support, and the catalyst having
    i. a proportion of its cobalt in reducible form, with this proportion expressed as Ω mass %, based on the total pre-reduction catalyst mass;
    ii. on fresh reduction, a mono-modal Gaussian metallic cobalt crystallite size distribution;
    iii. on fresh reduction, a metallic cobalt surface area, in $m^2$ per gram of catalyst, of from 0.14 Ω to 1.03 Ω; and
    iv. on fresh reduction, a catalyst geometry that ensures a stabilized Fischer-Tropsch synthesis effectiveness factor of 0.9 or greater.

2. A catalyst according to claim 1, wherein the metallic cobalt surface area of the catalyst, on fresh reduction, is, in $m^2$ per gram of catalyst, from 0.28 Ω to 0.89 Ω.

3. A catalyst according to claim 1, wherein the sizes of the majority of the cobalt crystallites are greater than 8 nm.

4. A catalyst according to claim 1, wherein the porous catalyst support is a calcined support.

5. A catalyst according to claim 1, wherein the catalyst support is a modified catalyst support comprising catalyst support particles coated with a modifying agent selected from the group consisting of Li, Na, K, Rb, Cs, Fr, Be, Mg, Ca, Sr, Ba, Ra and mixtures thereof.

6. A catalyst according to claim 5, wherein the modifying agent is barium so that the modified catalyst support comprises catalyst support particles coated with barium.

7. A catalyst according to claim 6, wherein the proportion of barium present on the catalyst support particles is from 0.2 mass % to 10 mass %, based on the pre-reduced catalyst mass.

8. A catalyst according to claim 1, wherein the catalyst support is a coated catalyst support comprising porous catalyst support particles coated with carbon.

9. A catalyst according to claim 8, wherein the amount of carbon present on the support is from 0.1 g carbon/100 g support to 40 g carbon/100 g support.

10. A process for preparing a cobalt based Fischer-Tropsch catalyst, which process comprises in a support impregnation stage, impregnating a particulate porous modified catalyst support with a cobalt salt, and partially drying the impregnated support, to obtain a partially dried impregnated support;

in a calcination stage, calcining the partially dried impregnated support to obtain a cobalt based catalyst precursor, with the precursor comprising calcined porous modified catalyst support particles containing cobalt oxide crystallites; and in a reduction stage, reducing the cobalt catalyst precursor, to obtain a cobalt based catalyst having (i) a proportion of its cobalt in reducible form, with this proportion expressed as $\Omega$ mass %, based on the total pre-reduced catalyst mass; (ii) on fresh reduction, a mono-modal Gaussian metallic cobalt crystallite size distribution; (iii) on fresh reduction, a metallic cobalt surface area, in $m^2$ per gram of catalyst, of from 0.14 $\Omega$ to 1.03 $\Omega$; and (iv) on fresh reduction, a catalyst geometry that ensures a stabilized Fischer-Tropsch synthesis effectiveness factor of 0.9 or greater.

11. A process for preparing a cobalt catalyst, which process comprises in a first step, in a support impregnation stage, impregnating a particulate porous catalyst support with a cobalt salt, and partially drying the impregnated support, and, in a calcination stage, calcining the partially dried impregnated support, to obtain a calcined material;

at least partially reducing the calcined material;

in a second step, in a support impregnation stage, impregnating the at least partially reduced material with a cobalt salt, and partially drying the impregnated material, and, in a calcination stage, calcining the partially dried impregnated material, to obtain the cobalt catalyst precursor, with the precursor comprising the calcined porous catalyst support with cobalt oxide crystallites present therein, and having a proportion of its cobalt in reducible form, with this proportion expressed as $\Omega$ mass %, based on the total precursor mass, wherein the precursor is capable of yielding, on fresh reduction thereof, a catalyst having a mono-modal Gaussian metallic cobalt crystallite size distribution; a metallic cobalt surface area from 0.14 $\Omega$ $m^2$ to 1.03 $\Omega$ $m^2$, per grain of catalyst; and a catalyst geometry that ensures a stabilized Fischer-Tropsch synthesis effectiveness factor of 0.9 or greater; and in a reduction stage, reducing the cobalt catalyst precursor, to obtain the supported cobalt catalyst having (i) a proportion of its cobalt in reducible form, with this proportion expressed as $\Omega$ mass %, based on the total pre-reduced catalyst mass; (ii) on fresh reduction a mono-modal Gaussian metallic cobalt crystallite size distribution; (iii) on fresh reduction, a metallic cobalt surface area, in $m^2$ per gram of catalyst, of from 0.14 $\Omega$ to 1.03 $\Omega$; and (iv) on fresh reduction, a catalyst geometry that ensures a stabilized Fischer-Tropsch synthesis effectiveness factor of 0.9 or greater.

12. A cobalt based catalyst precursor, which includes a porous catalyst support and cobalt oxide crystallites within the support, the precursor having a proportion of its cobalt in reducible form, with this proportion expressed as $\Omega$ mass %, based on the total precursor mass, wherein the precursor is capable of yielding, on fresh reduction thereof, a catalyst having a mono-modal Gaussian metallic cobalt crystallite size distribution; a metallic cobalt surface area, in $m^2$ per gram of catalyst, of from 0.14 $\Omega$ to 1.03 $\Omega$; and a catalyst geometry that ensures a stabilized Fischer-Tropsch synthesis effectiveness factor of 0.9 or greater.

13. A precursor according to claim 12, wherein the porous catalyst support is a calcined support.

14. A precursor according to claim 12, wherein the catalyst support is a modified catalyst support comprising catalyst support particles coated with a modifying agent selected from the group consisting of Li, Na, K, Rb, Cs, Fr, Be, Mg, Ca, Sr, Ba, Ra and mixtures thereof.

15. A precursor according to claim 14, wherein the modifying agent is barium so that the modified catalyst support comprises catalyst support particles coated with barium.

16. A precursor according to claim 15, wherein the proportion of barium present on the catalyst support particles is from 0.2% to 10% by mass, based on the pre-reduced catalyst mass.

17. A precursor according to claim 12, wherein the catalyst support is a coated catalyst support comprising porous catalyst support particles coated with carbon.

18. A precursor according to claim 17, wherein the amount of carbon present on the support is from 0.1 g carbon/100 g support to 40 g carbon/100 g support.

19. A process for preparing a cobalt based catalyst precursor, which process comprises in a support impregnation stage, impregnating a particulate porous modified catalyst support with a cobalt salt, and partially drying the impregnated support, to obtain a partially dried impregnated support; and in a calcination stage, calcining the partially dried impregnated support to obtain the cobalt based catalyst precursor, with the precursor comprising calcined porous modified catalyst support particles containing cobalt oxide crystallites, and the precursor having a proportion of its cobalt in reducible form, with this proportion expressed as $\Omega$ mass %, based on the total precursor mass, wherein the precursor is capable of yielding, on fresh reduction thereof, a catalyst having a mono-modal Gaussian metallic cobalt crystallite size distribution; a metallic cobalt surface area, in $m^2$ per gram of catalyst, of from $\Omega$ 0.14 to 1.03 $\Omega$; and a catalyst geometry that ensures a stabilized Fischer-Tropsch synthesis effectiveness factor of 0.9 or greater.

20. A process according to claim 19, wherein the cobalt salt is cobalt nitrate, and wherein the modified catalyst support is alumina, silica, silica-alumina, titania or magnesia, coated with one or more metals of Group IA and Group IIA of the Periodic Table of Elements as a modifying agent.

21. A process according to claim 19, wherein the cobalt salt is cobalt nitrate, and wherein the modified catalyst support is alumina, silica, silica-alumina, titania or magnesia, coated with carbon.

22. A process according to claim 19, wherein the support is a protected modified catalyst support containing silicon as a modifying component.

23. A process according to claim 19, wherein the cobalt based catalyst precursor is obtained by a 2-step slurry phase impregnation, drying and calcination process which includes, in a first step, impregnating the catalyst support with the cobalt salt, partially drying the impregnated support, and calcining the partially dried support, to obtain a calcined material, and thereafter, in a second step, impregnating the calcined material with the cobalt salt, partially drying the impregnated material, and calcining the partially dried material, to obtain the catalyst precursor.

24. A process according to claim 23, which includes partially reducing the calcined material prior to impregnating it with the cobalt salt.

25. A process according to claim 24, wherein the partial reduction of the calcined material is effected at a temperature of 100° C. to 300° C.

26. A process according to claim 24, wherein the partial reduction of the calcined material is effected by contacting the calcined material with a hydrogen and/or carbon monoxide containing gas.

27. A process according to claim 23, wherein during either or both of the two slurry phase impregnation steps, a water soluble precursor salt of palladium, platinum, or mixture thereof is added, as a dopant capable of enhancing the reducibility of the cobalt.

28. A process for preparing a cobalt catalyst precursor, which process comprises in a first step, in a support impregnation stage, impregnating a particulate porous catalyst support with a cobalt salt, and partially drying the impregnated support, and, in a calcination stage, calcining the partially dried impregnated support, to obtain a calcined material;

at least partially reducing the calcined material; and thereafter in a second step, in a support impregnation stage, impregnating the at least partially reduced material with a cobalt salt, and partially drying the impregnated material, and, in a calcination stage, calcining the partially dried impregnated material, to obtain the cobalt catalyst precursor, with the precursor comprising the calcined porous catalyst support with cobalt oxide crystallites present therein, and having a proportion of its cobalt in reducible form, with this proportion expressed as $\Omega$ mass %, based on the total precursor mass, wherein the precursor is capable of yielding, on fresh reduction thereof, a catalyst having a monomodal Gaussian metallic cobalt crystallite size distribution; a metallic cobalt surface area, in $m^2$ per gram of catalyst, of from 0.14 $\Omega$ to 1.03 $\Omega$; and a catalyst geometry that ensures a stabilized Fischer-Tropsch synthesis effectiveness factor of 0.9 or greater.

* * * * *

UNITED STATES PATENT AND TRADEMARK OFFICE
CERTIFICATE OF CORRECTION

PATENT NO.     : 6,835,690 B2
DATED          : December 28, 2004
INVENTOR(S)    : Peter Jacobus Van Berge et al.

It is certified that error appears in the above-identified patent and that said Letters Patent is hereby corrected as shown below:

Title page,
Item [73], Assignee, "Technology" should read -- Technology (Proprietary) --.

Signed and Sealed this

Nineteenth Day of April, 2005

JON W. DUDAS
*Director of the United States Patent and Trademark Office*